United States Patent
Kamatani et al.

(10) Patent No.: US 10,193,084 B2
(45) Date of Patent: Jan. 29, 2019

(54) 2,2'-BIBENZO[D]IMIDAZOLIDENE COMPOUND HAVING HETEROMONOCYCLIC GROUPS AT THE 1-, 1'-, 3- AND 3'- POSITIONS, AND ORGANIC LIGHT-EMITTING ELEMENT AND DISPLAY DEVICE CONTAINING THE SAME

(71) Applicant: CANON KABUSHIKI KAISHA, Tokyo (JP)

(72) Inventors: Jun Kamatani, Tokyo (JP); Yosuke Nishide, Kawasaki (JP); Hirokazu Miyashita, Tokyo (JP); Naoki Yamada, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/569,675

(22) PCT Filed: Mar. 24, 2016

(86) PCT No.: PCT/JP2016/001702
§ 371 (c)(1),
(2) Date: Oct. 26, 2017

(87) PCT Pub. No.: WO2016/174813
PCT Pub. Date: Nov. 3, 2016

(65) Prior Publication Data
US 2018/0294418 A1    Oct. 11, 2018

(30) Foreign Application Priority Data

Apr. 30, 2015    (JP) .................. 2015-093571

(51) Int. Cl.
| | |
|---|---|
| *C07D 401/14* | (2006.01) |
| *H01L 51/00* | (2006.01) |
| *C07D 403/14* | (2006.01) |
| *C07D 409/14* | (2006.01) |
| *G03G 15/04* | (2006.01) |
| *G09G 3/3208* | (2016.01) |
| *H01L 51/50* | (2006.01) |
| *H01L 27/146* | (2006.01) |

(52) U.S. Cl.
CPC ........ *H01L 51/0072* (2013.01); *C07D 401/14* (2013.01); *C07D 403/14* (2013.01); *C07D 409/14* (2013.01); *G03G 15/04036* (2013.01); *H01L 51/0067* (2013.01); *H01L 51/0068* (2013.01); *G03G 2215/0409* (2013.01); *G09G 3/3208* (2013.01); *H01L 27/14643* (2013.01); *H01L 51/5092* (2013.01)

(58) Field of Classification Search
CPC ............ H01L 51/0072; H01L 51/0067; H01L 51/0068; H01L 27/14643; H01L 51/5092; C07D 401/14; C07D 403/14; C07D 409/14; G03G 15/04036; G09G 3/3208
See application file for complete search history.

(56) References Cited

U.S. PATENT DOCUMENTS

| | | | | |
|---|---|---|---|---|
| 9,842,997 | B2* | 12/2017 | Kamatani | ........... H01L 51/0067 |
| 9,846,385 | B2* | 12/2017 | Kamatani | ........ G03G 15/04054 |
| 9,882,148 | B2* | 1/2018 | Kamatani | ............ C07D 235/20 |
| 2007/0267970 | A1 | 11/2007 | Yamamoto | |
| 2012/0146012 | A1 | 6/2012 | Limmert | |
| 2012/0193612 | A1 | 8/2012 | Chun | |
| 2015/0162545 | A1* | 6/2015 | Kamatani | ........... H01L 51/0067 |
| | | | | 257/40 |
| 2015/0162549 | A1* | 6/2015 | Kamatani | ........ G03G 15/04054 |
| | | | | 257/40 |
| 2017/0155059 | A1* | 6/2017 | Kamatani | ............ C07D 235/20 |
| 2017/0263870 | A1* | 9/2017 | Kamatani | ............ C07D 235/20 |
| 2018/0108691 | A1* | 4/2018 | Kamatani | ............. H01L 51/005 |

FOREIGN PATENT DOCUMENTS

| | | |
|---|---|---|
| JP | 2016-102078 A | 6/2016 |
| WO | 2015-198579 A1 | 12/2015 |

OTHER PUBLICATIONS

Bourson, Jean, "No. 596—Studies in benzimidazole series III. Action of bases on 1,3-diphenyl benzimidazolium salts," Bulletin of the Chemical Society of France, Oct. 1971, 3541-3547.

D. Vasudevan, H. Wendt, "Electroreduction of Oxygen in Aprotic Media", Journal of Electroanalytical Chemistry 192 (1995), pp. 69-74.

Mareva Fevre, et al., "Imidazolium Hydrogen Carbonates versus Imidazolium Carboxylates as Organic Precatalysts for N-Heterocyclic Carbene Catalyzed Reactions", Journal of Organic Chemistry, 2012, vol. 77, No. 22, pp. 10135-10144.

F. Ekkehardt Hahn, et al., "N,N'-Bis(2,2-dimethylpropyl)benzimidazolin-2-ylidene: A Stable Nucleophilic Carbene Derived from Benzimidazole", Chemistry—A European Journal, 1999, vol. 5, No. 6, pp. 1931-1935.

(Continued)

*Primary Examiner* — Alexander R Pagano
(74) *Attorney, Agent, or Firm* — Canon U.S.A.Inc., IP Division

(57) ABSTRACT

A 2,2'-bibenzo[d]imidazolidene compound expressed by the following general formula (1). In general formula (1), $Ar_1$ to $Ar_4$ each represent a substituted or unsubstituted heteromonocyclic group. $R_1$ to $R_8$ each represent a hydrogen atom or a substituent.

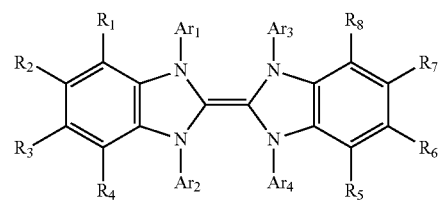

20 Claims, 3 Drawing Sheets

(56) References Cited

OTHER PUBLICATIONS

Farman Ullah, et al., "Annulated N-Heterocyclic Carbenes: 1,3-Ditolylphenanthreno[9,10-d]imidazol-2-ylidene and Transition Metal Complexes Thereof", Organometallics 2009, vol. 28, No. 8, pp. 2441-2449.

Hasan Kucukbay, et al., "Synthesis, Antibacterial and Antifungal Activities of Electron-rich Olefins Derived Benzimidazole Compounds", IL Farmaco, 2003, vol. 58, No. 6, pp. 431-437.

* cited by examiner (a)

(b)

2,2'-BIBENZO[D]IMIDAZOLIDENE COMPOUND HAVING HETEROMONOCYCLIC GROUPS AT THE 1-, 1'-, 3- AND 3'- POSITIONS, AND ORGANIC LIGHT-EMITTING ELEMENT AND DISPLAY DEVICE CONTAINING THE SAME

CROSS-REFERENCE TO RELATED APPLICATIONS

This application is a National Stage filing of International Application No. PCT/JP2016/001702 filed Mar. 24, 2016, which claims the benefit of Japanese Patent Application No. 2015-093571, filed Apr. 30, 2015, the disclosures of each of which are hereby incorporated by reference herein in their entirety.

TECHNICAL FIELD

The present invention relates to a 2,2'-bibenzo[d]imidazolidene compound having heteromonocyclic groups at the 1-, 1'-, 3- and 3'-positions, and an organic light-emitting element and a display device, an image information processing apparatus, a lighting device, an image forming apparatus, and an exposure device that contain the compound.

BACKGROUND ART

An organic light-emitting element includes an anode and a cathode, and an organic compound layer between the anode and the cathode. The organic light-emitting element emits light by recombination of holes injected from the anode and electrons injected from the cathode in a luminescent layer that is a type of the organic compound layer. Recent significant advances in development of organic light-emitting elements have been achieving thin, lightweight light-emitting devices that can emit a variety of emission wavelengths and respond rapidly at a low driving voltage.

In order to reduce the driving voltage of an organic light-emitting element, it is effective to improve the electron injectability in the organic light-emitting element. It is known that a compound containing a metal atom is used to improve the electron injectability.

NPLs 1 and 2 disclose processes for synthesizing compounds 1-A and 1-B. These compounds have not been described as compounds used in organic electric field elements.

[Chem. 1]

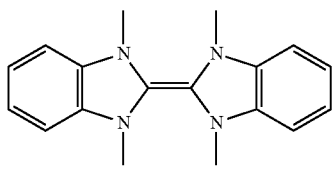

1-A

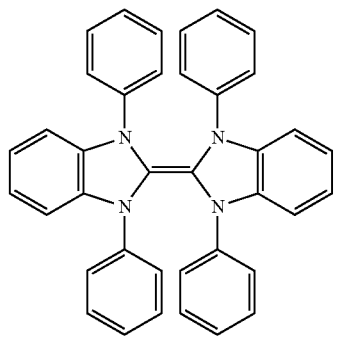 [SMILES: c1ccc(N2C(=C3N(c4ccccc4)c4ccccc4N3c3ccccc3)N(c3ccccc3)c3ccccc32)cc1]

1-B

It is known that a compound containing a metal atom is used in the electron injection layer of organic light-emitting elements. Although such an electron injection layer is advantageous in terms of electron injectability, it is reactive with water and is accordingly likely to reduce the lifetime of the element.

The compounds disclosed in NPLs 1 and 2 are unstable to oxidation in the air and are accordingly difficult to handle in the air.

CITATION LIST

Non Patent Literature

NPL 1: F. Ekkehardt Hahn, "N,N'-Bis(2,2-dimethylpropyl) benzimidazolin-2-ylidene: A Stable Nucleophilic Carbene Derived from Benzimidazole", Chemistry-A European Journal (1999), 5, (6), 1931-1935

NPL 2: Jean Bourson, "Benzimidazoles. III. Action of bases on 1,3-diphenylbenzimidazolium salts", Bulletin de la Societe Chimique de France (1971), (10), 3541-7

SUMMARY OF INVENTION

The present invention provides a 2,2'-bibenzo[d]imidazolidene compound having heteromonocyclic groups at the 1-, 1'-, 3-, 3'-positions thereof, which is stable to oxidation in the air because of the presence of the heteromonocyclic groups.

According to an aspect of the present invention, there is provided a 2,2'-bibenzo[d]imidazolidene compound expressed by the following general formula (1).

[Chem. 2]

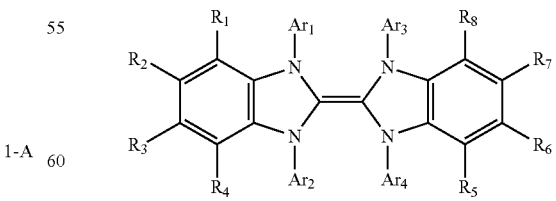

(1)

In general formula (1), $Ar_1$ to $Ar_4$ each represent a substituted or unsubstituted heteromonocyclic group.

$R_1$ to $R_8$ each represent a hydrogen atom or a substituent. The substituent is selected from the group consisting of halogen atoms, alkyl groups having a carbon number in the range of 1 to 8, and substituted or unsubstituted aromatic hydrocarbon groups.

Advantageous Effects of Invention

Since the 2,2'-bibenzo[d]imidazolidene compound of the present invention has heteromonocyclic groups at the 1-, 1'-, 3-, 3'-positions, the compound is stable to oxidation in the air.

Further features of the present invention will become apparent from the following description of exemplary embodiments with reference to the attached drawings.

DESCRIPTION OF EMBODIMENTS

Figure 1:
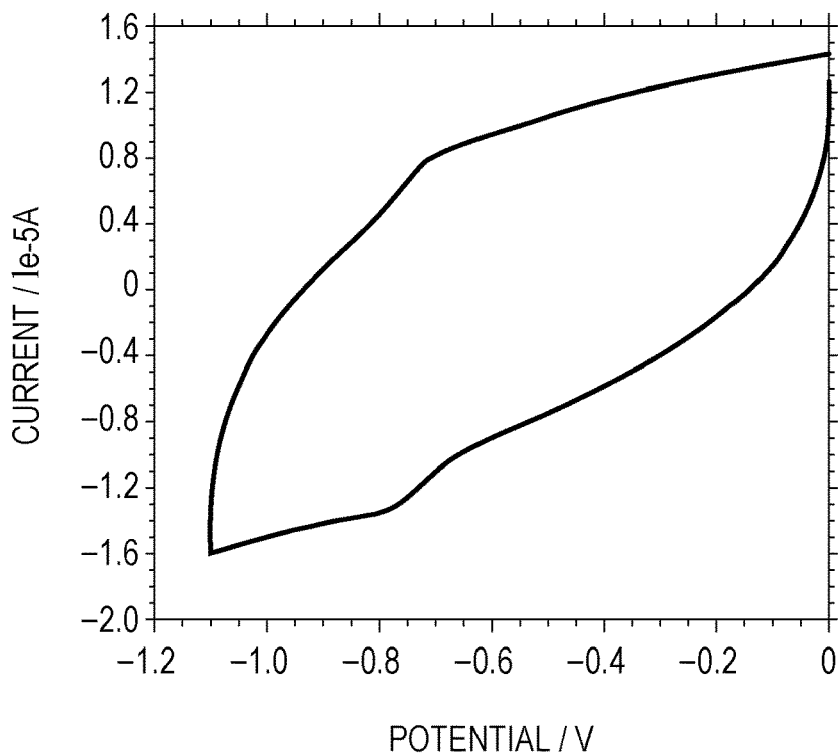
FIG. 1 is a cyclic voltammogram of an organic compound according to an embodiment of the present invention.

The present invention provides a 2,2'-bibenzo[d]imidazolidene compound expressed by the following general formula (1). This compound is less reactive with oxygen and moisture in the air and can therefore exist stably because of the presence of the heteromonocyclic groups at the 1-, 1'-, 3- and 3'-positions thereof.

In the following description, the 2,2'-bibenzo[d]imidazolidene compound having heteromonocyclic groups at the 1-, 1'-, 3- and 3'-positions may be referred to as the present organic compound.

The present organic compound is expressed by the following general formula (1).

[Chem. 3]

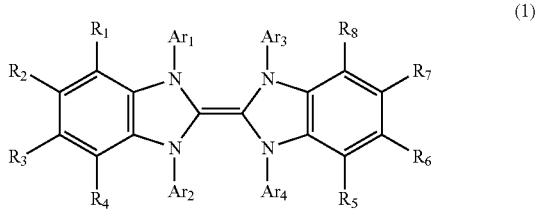

(1)

In general formula (1), $Ar_1$ to $Ar_4$ each represent a substituted or unsubstituted heteromonocyclic group. $R_1$ to $R_8$ each represent a hydrogen atom or a substituent. The substituent is selected from the group consisting of halogen atoms, alkyl groups having a carbon number in the range of 1 to 8, and substituted or unsubstituted aromatic hydrocarbon groups.

Each heteromonocyclic group represented by $Ar_1$ to $Ar_4$ may be a 6-membered aromatic ring including carbon and nitrogen atoms or a 5-membered ring including a carbon atom and any of nitrogen, sulfur, and oxygen atoms.

More specifically, examples of the heteromonocyclic groups include pyridyl, pyrazyl, pyrimidyl, pyrimididazoyl, triazyl, pyrrole, furanyl, thienyl, imidazole, pyrazole, oxazole, thiazole, imidazoline, and thiazine.

Examples of the aromatic hydrocarbon group include phenyl, naphthyl, phenanthrenyl, chrysenyl, pyrenyl, fluorenyl, and fluoranthenyl. Phenyl is particularly advantageous.

The heteromonocyclic group may be substituted. The substituent of the heteromonocyclic group is selected from the group consisting of alkyl groups having a carbon number in the range of 1 to 4; aromatic hydrocarbon groups, such as phenyl, naphthyl, phenanthryl, and fluorenyl; and halogen atoms, such as fluorine, chlorine, bromine, and iodine. If the substituent is a halogen atom, fluorine is advantageous.

If the substituent is an aromatic hydrocarbon group, the aromatic hydrocarbon group may be substituted by an alkyl group. Advantageously, the carbon number of this alkyl group is in the range of 1 to 4.

The alkyl groups having a carbon number in the range of 1 to 4 include methyl, ethyl, n-propyl, isopropyl, n-butyl, isobutyl, sec-butyl, and tert-butyl.

The halogen atoms represented by $R_1$ to $R_8$ include fluorine, chlorine, bromine, and iodine. Fluorine is advantageous.

Examples of the alkyl groups represented by $R_1$ to $R_8$ having a carbon number in the range of 1 to 8 include methyl, ethyl, n-propyl, isopropyl, n-butyl, isobutyl, sec-butyl, tert-butyl, n-pentyl, n-hexyl, and n-octyl.

The phenyl group represented by $R_1$ to $R_8$ may be substituted. In this instance, the substituent is selected from the group consisting of alkyl groups having a carbon number in the range of 1 to 4; aromatic hydrocarbon groups, such as phenyl, naphthyl, phenanthryl, and fluorenyl; and halogen atoms, such as fluorine, chlorine, bromine, and iodine. If the substituent is a halogen atom, fluorine is advantageous.

Characteristics of the Present Organic Compound

The present organic compound has heteromonocyclic groups at the 1-, 1'-, 3- and 3'-positions of the 2,2'-benzo[d]imidazolidene skeleton. By providing the active nitrogen atoms of the 1,1',3,3'-tetrahydro-2,2'-bibenzo[d]imidazolidene skeleton, which has a low oxidation potential and is thus unstable, with heteromonocyclic groups, the stability of the compound can be improved. The term low oxidation potential means that the actual value of the oxidation potential is low.

In addition, the 1,1',3,3'-tetrahydro-2,2'-bibenzo[d]imidazolidene skeleton has a high electron injectability.

The present 2,2'-bibenzo[d]imidazolidene compound having these two characteristic features is less reactive with oxygen and water in the air and thus exhibits both a high electron injectability and a high stability.

Although organic compounds containing a metal atom exhibit high electron injectability, metal-free organic compounds are advantageous as the organic compound used in organic electric field elements. The advantage of using a metal-free organic compound in the organic electric field element is that it is stable to water. Known alkali metal-containing compounds such as lithium fluoride and quinolinol lithium complexes are reactive with water. Therefore, if such a compound is used in an organic electric filed element, carriers can be efficiently injected from an electrode. The compound is however likely to be ionized by external moisture or the like. This is a cause of instability of the element.

The use of a metal-free organic compound enables a stable element to be provided.

Organic compounds used as the electron-injecting material desirably have shallow HOMO (highest occupied molecular orbital) levels close to the energy level of the cathode. The term "shallow HOMO level" mentioned herein means that the absolute value of the HOMO level is small, and implies that it is closer to the vacuum level. A shallow HOMO level is substantially synonymous with a low first oxidation potential in cyclic voltammetry (CV).

The use of a compound having a shallow HOMO level reduces the energy barrier of electrons to be injected from the cathode to an electron conduction band. From the viewpoint of functioning as an electron-injecting material, the organic compound desirably has a relatively low first oxidation potential. For example, the first oxidation potential is 0 V or less (vs. Fc/Fc$^+$), such as −0.7 V or less (vs. Fc/Fc$^+$). The present compound, however, can exhibit satisfactory properties as an electron-injecting material because of the presence of the heteromonocyclic groups even though the first oxidation potential of the compound is −0.6 V or less (vs. Fc/Fc$^+$). The expression "vs. Fc/Fc$^+$" represents that the first oxidation potential is a value relative to the oxidation-reduction potential of ferrocene.

In an organic light-emitting element including an electron injection layer containing a compound having a shallower HOMO level, that is, having a lower first oxidation potential, electrons can be more efficiently injected from the cathode to the electron injection layer.

Organic compounds having a first oxidation potential higher than the oxidation-reduction potential of oxygen are stable to oxygen. Hence, it is advantageous that the present organic compound has a higher first oxidation potential than the oxidation-reduction potential of oxygen. The oxidation-reduction potential ($O_2/O_2^-$) of oxygen is −1.22 V (vs. Fc/Fc$^+$) in DMF (dimethylformamide) (see D. Vasudevan "Electroreduction of Oxygen in Aprotic Media" Journal of Electroanalytical Chemistry 192 (1995) 69-74).

Hence, the first oxidation potential of the organic compound in DMF is desirably in the range of −1.20 V to 0.00 V (vs. Fc/Fc$^+$), and more desirably in the range of −1.20 V to −0.70 V (vs. Fc/Fc$^+$). When the first oxidation potential is within such a range, the organic compound is stable to oxygen and superior in electron injectability.

In addition, in the case of using the present organic compound, the unpaired electrons of the heteroatoms act on the electrode. Consequently, electrons may be efficiently injected even if the first oxidation potential is −0.70 V or more. In such a case, the first oxidation potential is desirably in the range of −1.20 V to −0.60 V (vs. Fc/Fc$^+$).

Oxidation potential can be measured by cyclic voltammetry (CV). More specifically, oxidation potential can be estimated from the peak of oxidation current in a CV curve.

FIG. 1 is a cyclic voltammogram of Exemplified Compound A1, which is an organic compound of the present invention.

Exemplified Compound A1 exhibits a reversible oxidation-reduction reaction as shown in FIG. 1 and is thus stable to oxidation and reduction. The oxidation-reduction potential estimated from the peak of oxidation potential is −1.1 V, which is within the range of −1.20 V to 0.00 V.

Exemplified Compound A14 has a low oxidation potential and accordingly can act as a donor. When this compound is mixed a compound capable of acting as an acceptor, a charge transfer complex is formed. It is expected that carriers can be easily injected from an electrode in an organic light-emitting element by using this charge transfer complex in an organic compound layer in contact with the electrode.

On the other hand, Comparative Compounds 3 and 4 did not exhibit an oxidation potential peak of about −1.0 V when measured after being allowed to stand in the air. This suggests that the intrinsic property of these compounds has been lost by oxidation. Comparative Compound 3 has the same structure as Compound 1-B cited in the Background Art, and Comparative Compound 4 has the same structure as Compound 1-A.

Stabilities to water of the present organic compound and Comparative Examples were examined to estimate the reactivity of these compounds with water in the air. Powders of alkali metal containing compounds (lithium fluoride and cesium fluoride), other comparative compounds, and organic compounds according to the present invention were allowed to stand in a high-humidity environment of 95% for 30 minutes, and then the changes thereof were visually compared. The results are shown in Table 1.

TABLE 1

| | | Reactivity |
|---|---|---|
| Organic compound 1 of the invention | (structure) | Not changed |

TABLE 1-continued

| | | Reactivity |
|---|---|---|
| Organic compound 2 of the invention | (structure) | Not changed |
| Comparative Compound 1 | LiF | Deliquesced slightly |
| Comparative Compound 2 | CsF | Deliquesced |
| Comparative Compound 3 | (structure) | Turned red |
| Comparative Compound 4 | (structure) | Deliquesced and turned black |

As shown in Table 1, the present organic compounds did not change, while Comparative Compounds 1 to 4 deliquesced or turned red or black.

Comparative Compound 4 oxidized faster than Comparative Compound 3 and turned black while being deliquescing. This is probably because the substituents bound to the nitrogen atoms of Comparative Compound 4 are methyl groups having a small excluded volume.

The present organic compound has a stability improved by providing unstable sites of the 1,1',3,3'-tetrahydro-2,2'-bibenzo[d]imidazolidene skeleton with heteromonocyclic groups to increase the oxidation potential.

The electron density of each site of the 1,1',3,3'-tetraphenyl-2,2'-bibenzo[d]imidazolidene skeleton was estimated by a molecular orbital calculation. The calculation was performed as below. For calculation for the molecular structures in the electronic ground state and electrically excited state, a commercially available electronic state calculation software program Gaussian 03 Revision D. 01 was used. In this operation, Density Functional Theory was adopted as quantum chemical calculation, and B3LYP was used for the functional. The basis function was 6-31G(d).

As shown in Chemical Structural Formula (3), the nitrogen atoms, which are considered to be active, had a large negative charge. Sites of the chemical structure symmetrical each other have the same value.

[Chem. 4]

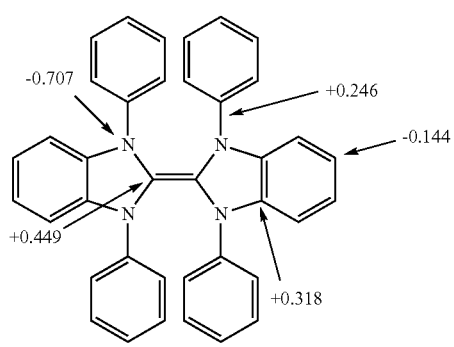

(3)

It is though that the 1-, 1'-, 3- and 3'-positions having the largest negative charge are the cause of low stability. The present organic compound is therefore provided with heteromonocyclic groups as substituents, thereby being made stable in the air.

The compound having 3-pyridine as substituents at the 1-, 1'-, 3- and 3'-positions, expressed by the following structural formula (4), that is, 1,1',3,3'-tetra(pyridine-3-yl)-2,2'-bibenzo[d]imidazolidene, is stable in the air. While 1,1',3,3'-tetraphenyl-2,2'-bibenzo[d]imidazolidene expressed by formula (3) has an oxidation potential of −0.92 V, 1,1',3,3'-tetra(pyridine-3-yl)-2,2'-bibenzo[d]imidazolidene has an oxidation potential of −0.68 V. The oxidation potential of 1,1',3,3'-tetra(pyridine-3-yl)-2,2'-bibenzo[d]imidazolidene is 0.24 V higher than that of the other. The oxidation potential is increased due to the presence of the heteromonocyclic groups. This is probably the reason why the stability of the compound is improved.

[Chem. 5]

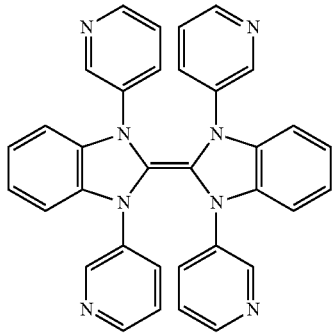

(4)

The present compound has an increased oxidation potential because of the presence of heteromonocyclic groups and is thus stable. In addition, the heteromonocyclic groups help the compound exhibit good injectability of carriers from an electrode. Since the present organic compound has an oxidation potential in the range of −0.75 V to −0.60 V, the compound can be stable in the air and exhibits high electron injectability.

Accordingly, a 2,2'-bibenzo[d]imidazolidene compound having heteromonocyclic groups at the 1-, 1'-, 3- and 3'-positions is more stable to water than alkali metal salts and alkali metals. By using such a 2,2'-bibenzo[d]imidazolidene compound, a stable organic electric filed element can be provided.

It can be checked by subjecting the organic compound layer to TOF-SIMS (Time-of-Flight Secondary Ion Mass Spectrometry) or the like whether or not an organic light-emitting element contains the present organic compound. Alternatively, the organic compound extracted from the organic light-emitting element may be measured with IR or UV or by NMR.

Exemplification of 2,2'-bibenzo[d]imidazolidene Compound Having heteromonocyclic Groups at the 1-, 1'-, 3- and 3'-Positions There will be shown exemplary structures of the 2,2'-bibenzo[d]imidazolidene compound having heteromonocyclic groups at the 1-, 1'-, 3- and 3'-positions. In the following formulas, tBu represents a tertiary butyl group.

[Chem. 6]

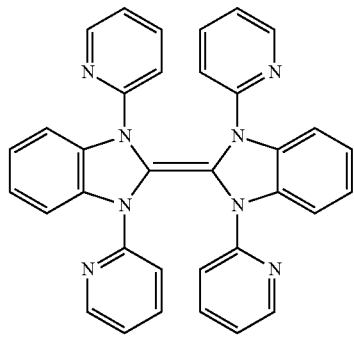

A1

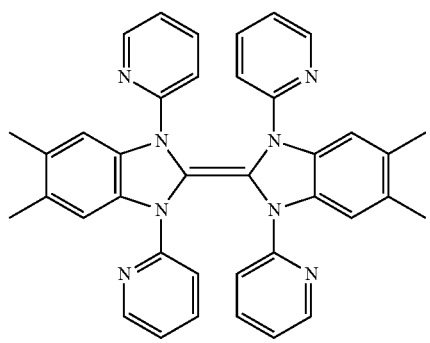

A2

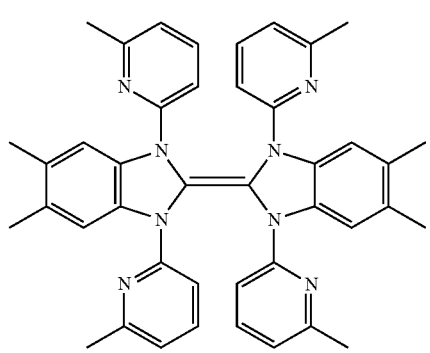

A3

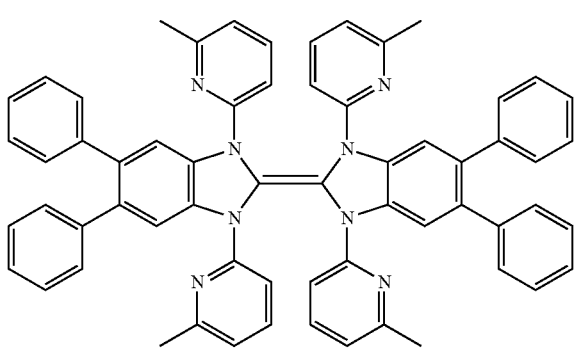

A4

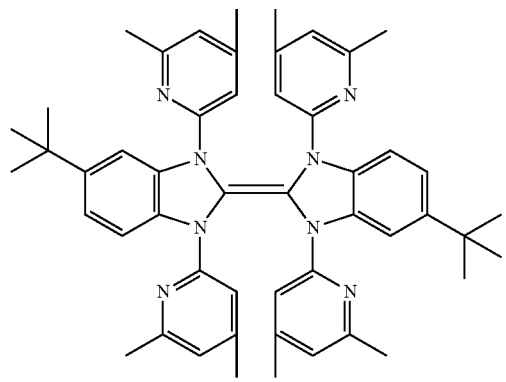
A5
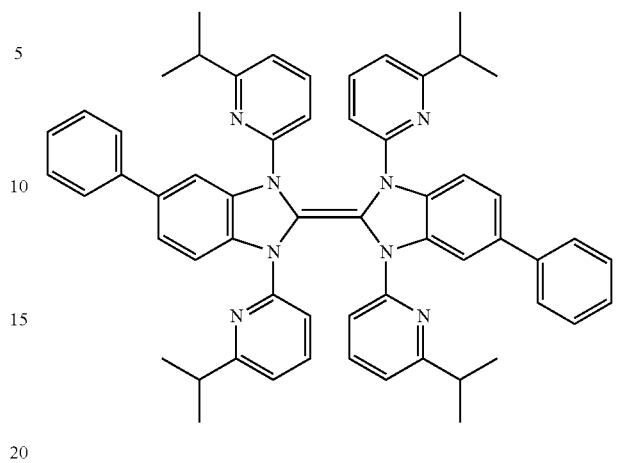
A8
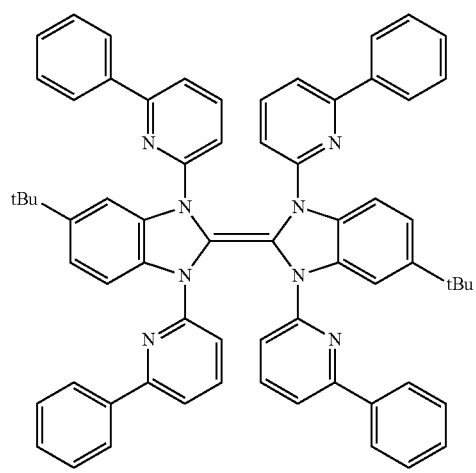
A6
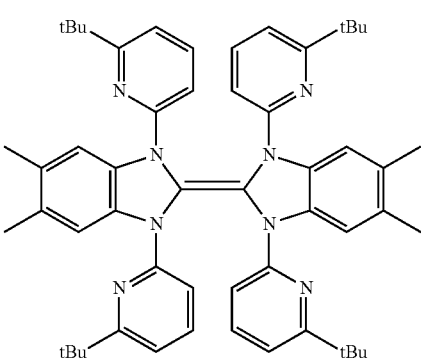
A9
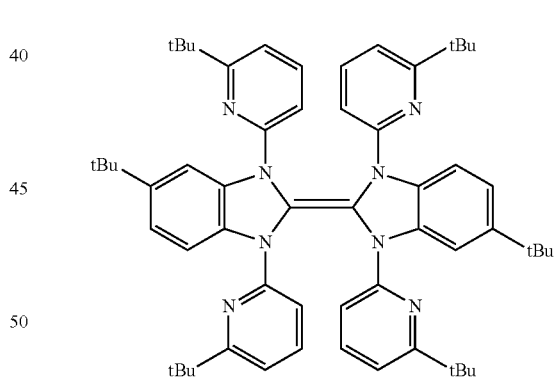
A10
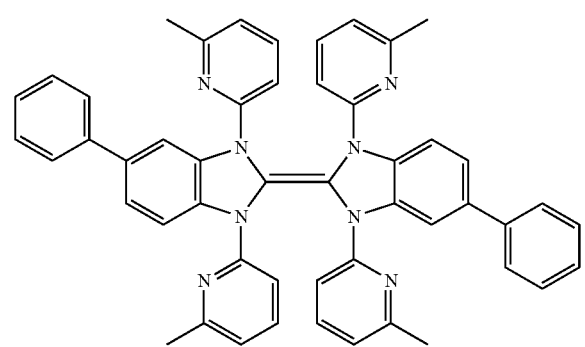
A7
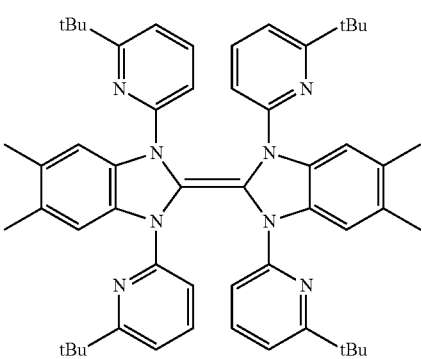
A11

-continued
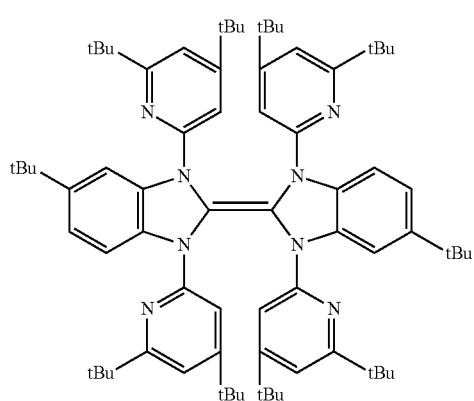
A12
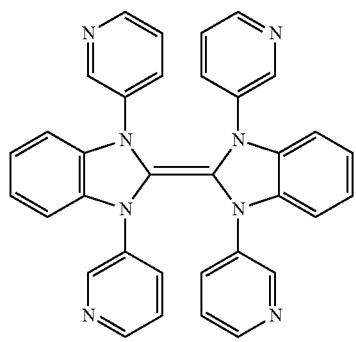
A13
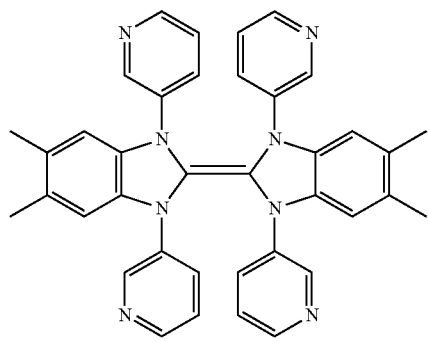
A14
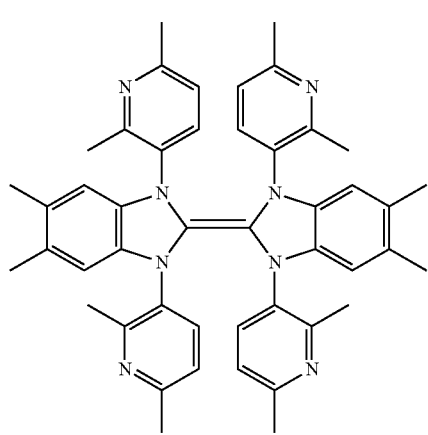
A15
-continued
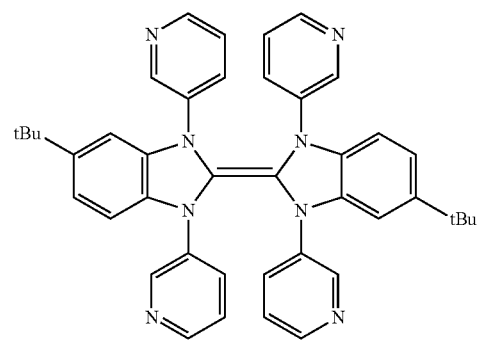
A16
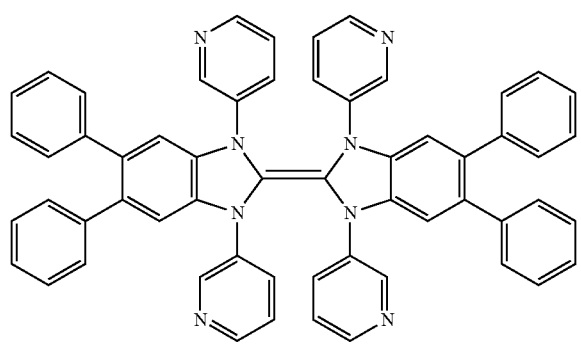
A17
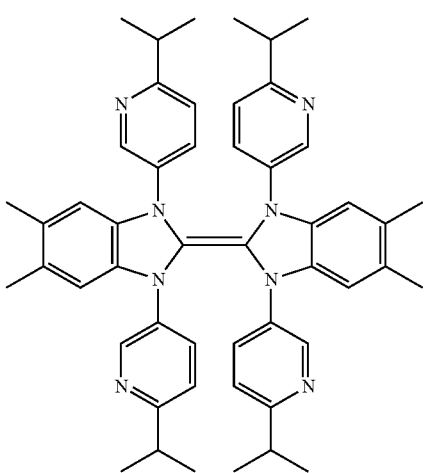
A18
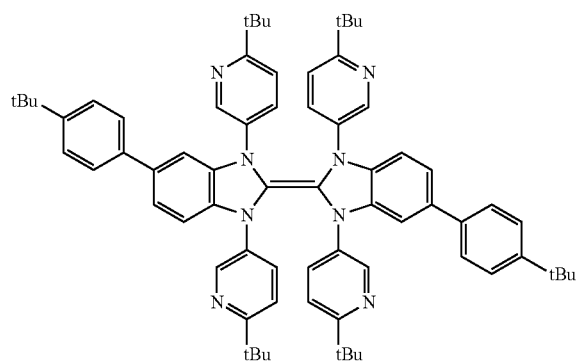
A19

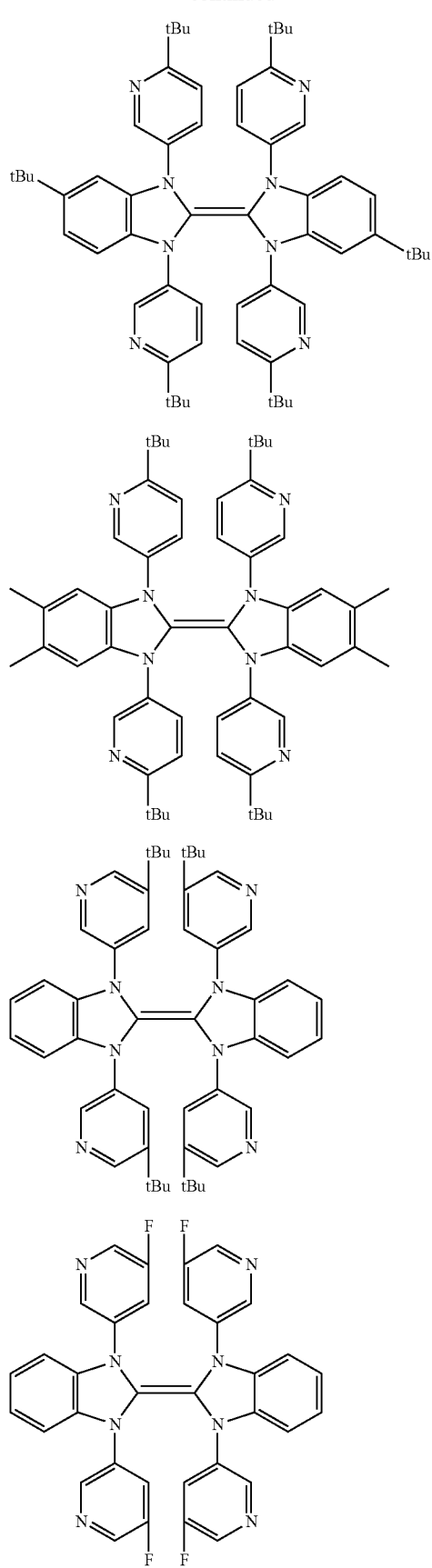
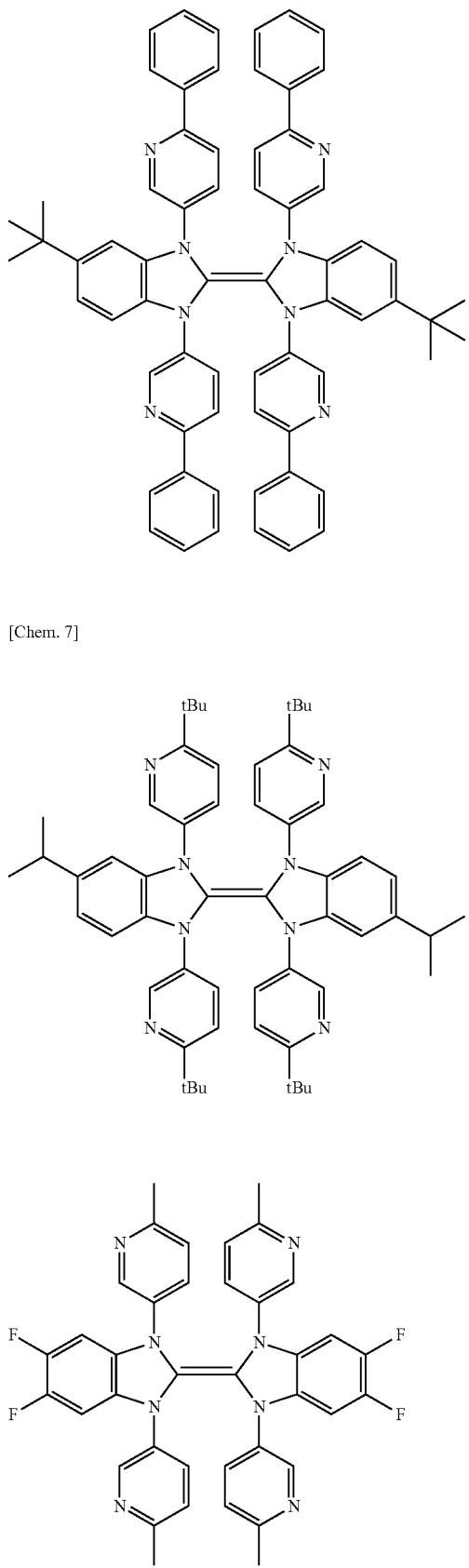

A27
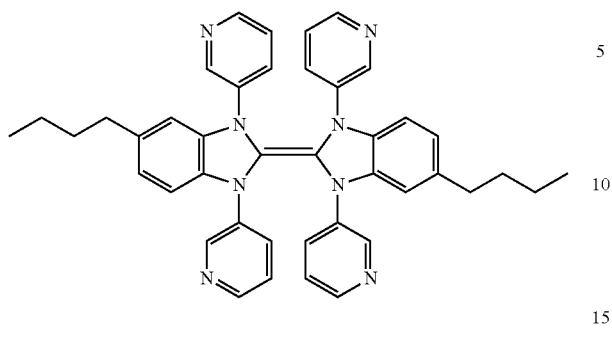
A31
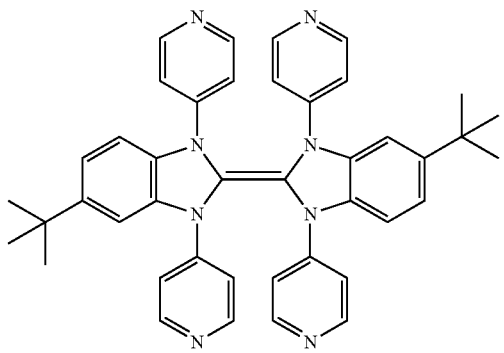
A28
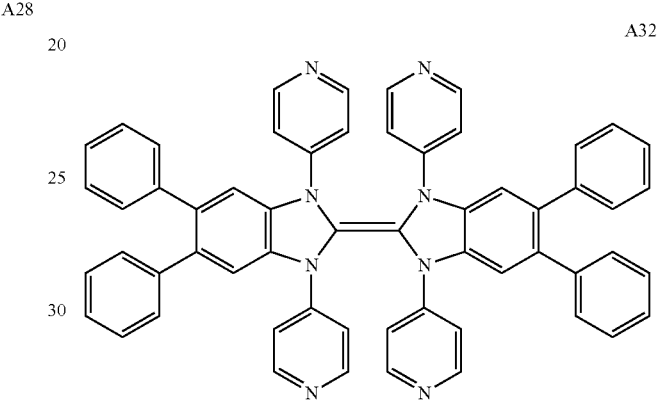
A29
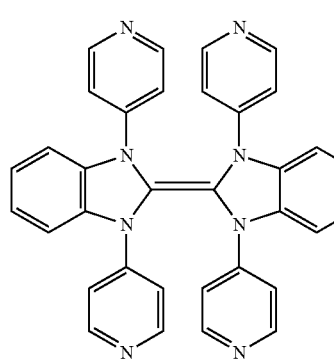
A33
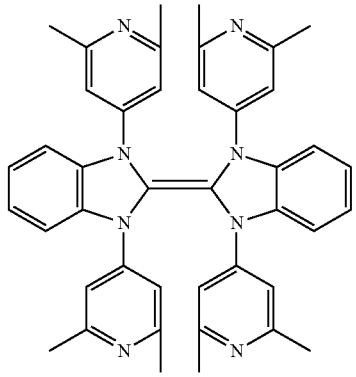
A30
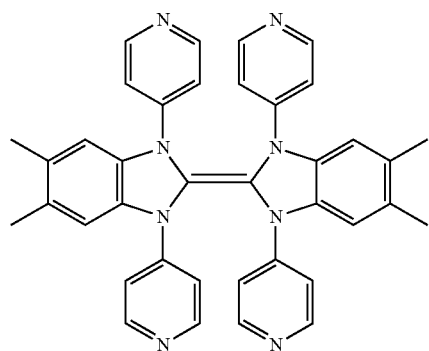
A34
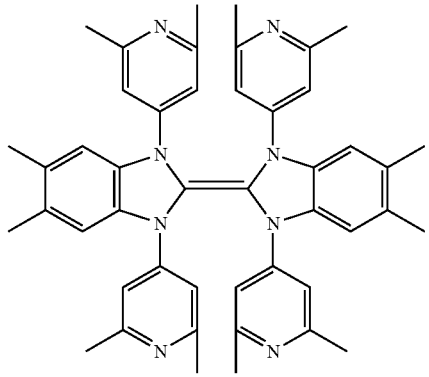

A35
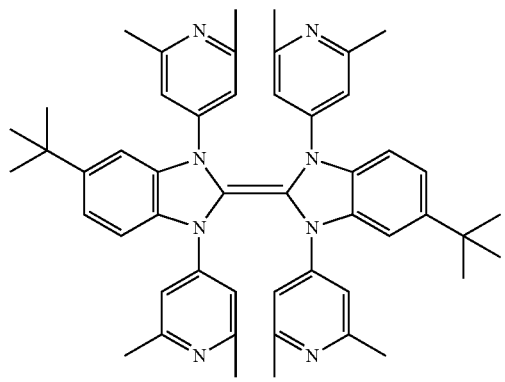
A36
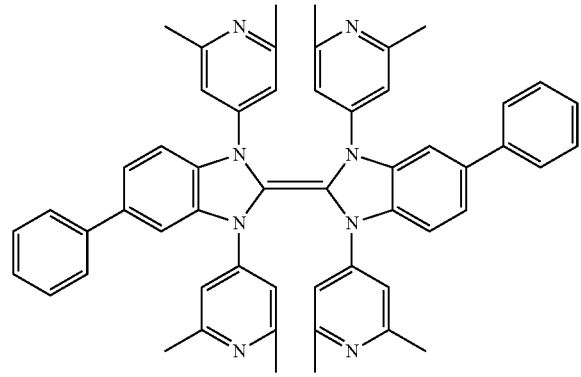
A37
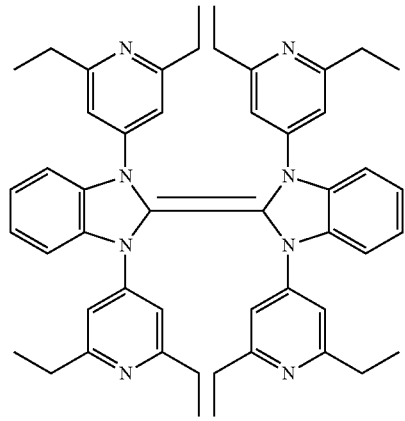
A38
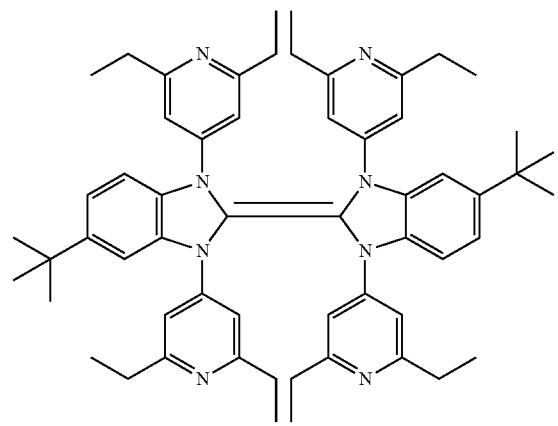
A39
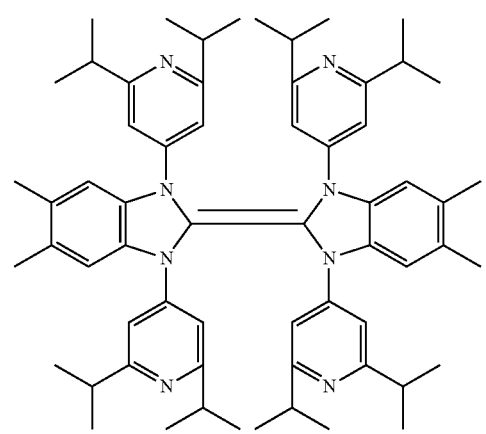
A40
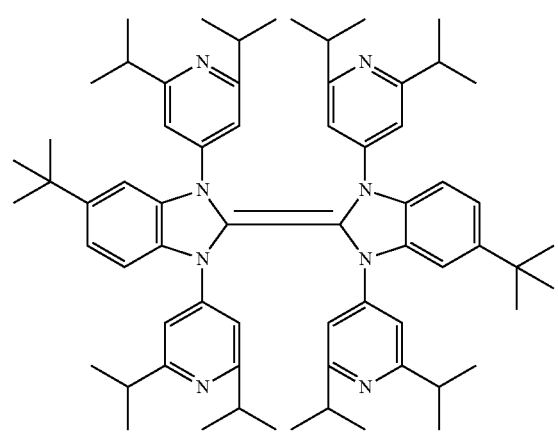

A41 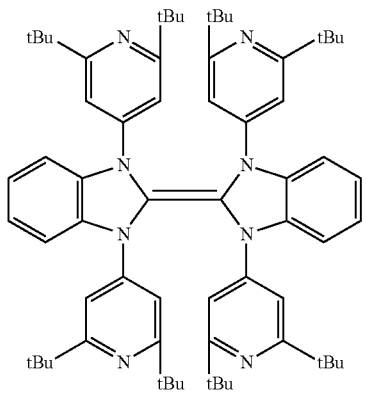
A42 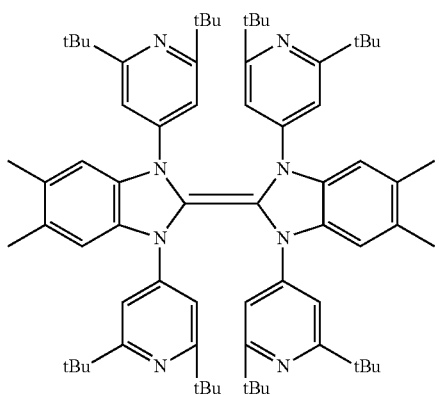
A43 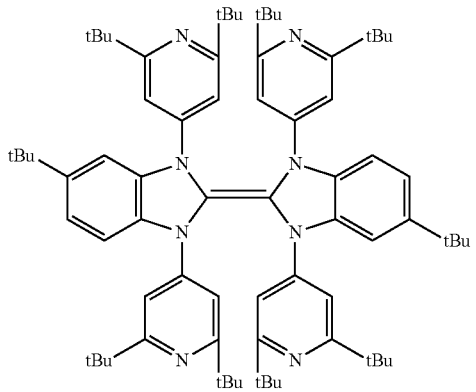
A44 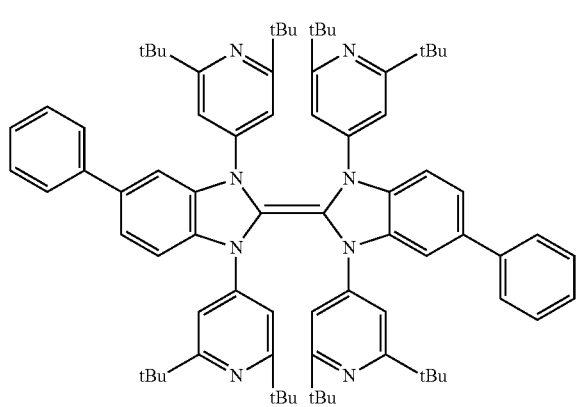
A45 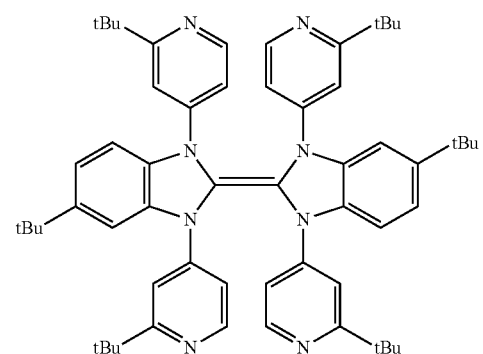
A46 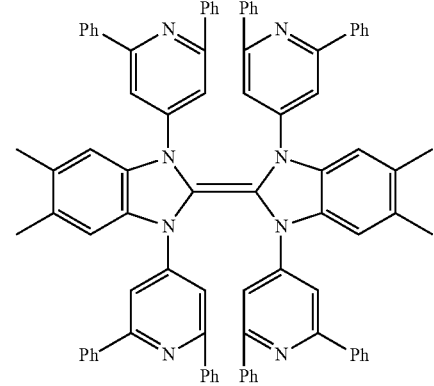
A47 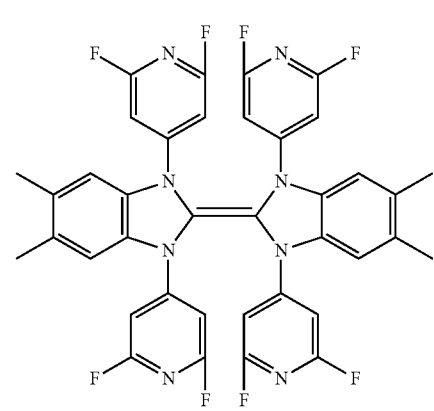
A48 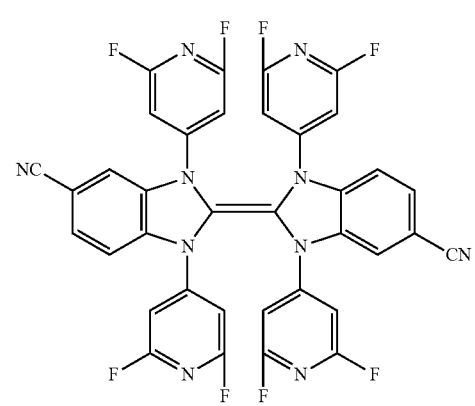

[Chem. 8]
B1 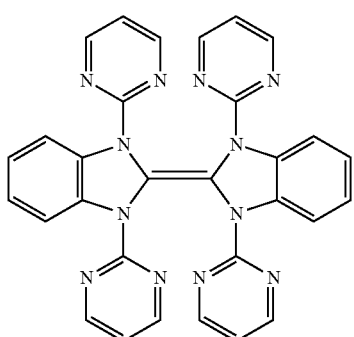
B2 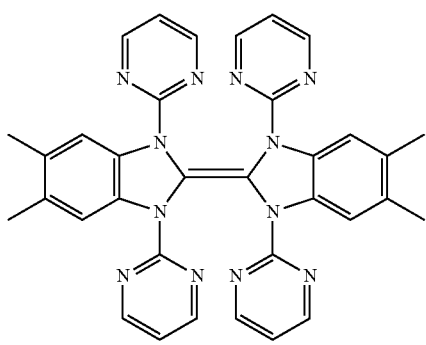
B3 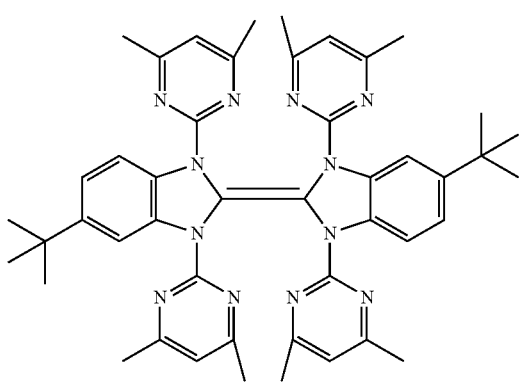
B4 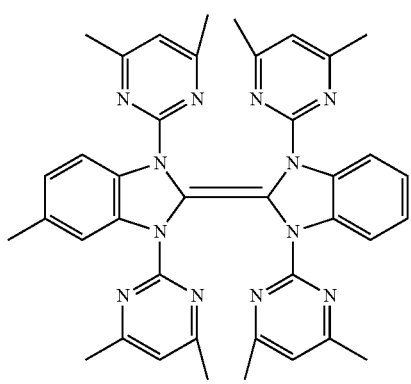
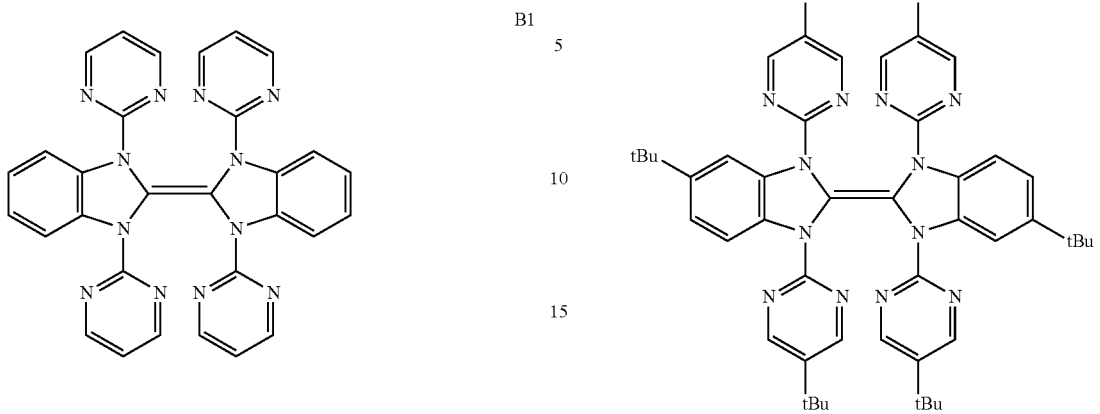
B6 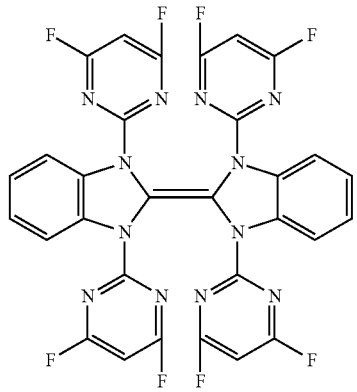
B7 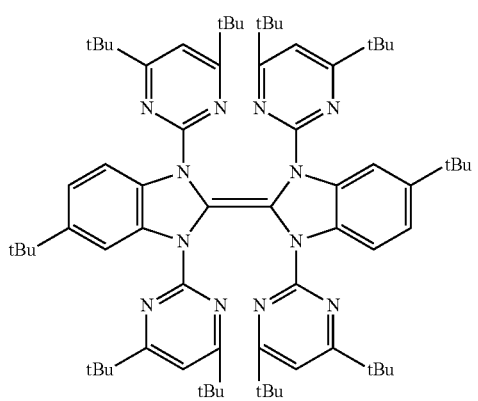
B8 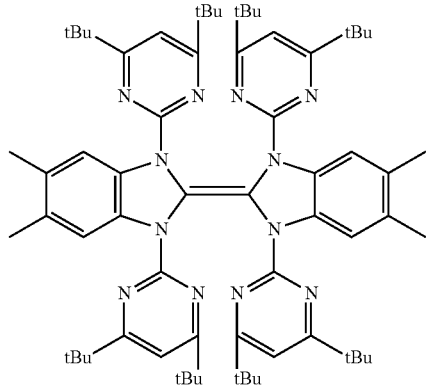

-continued
B9
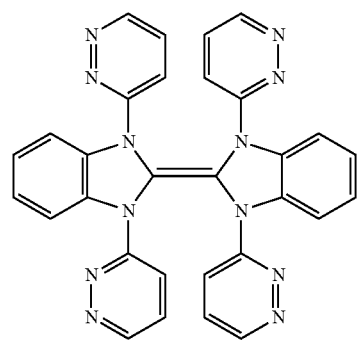
B10
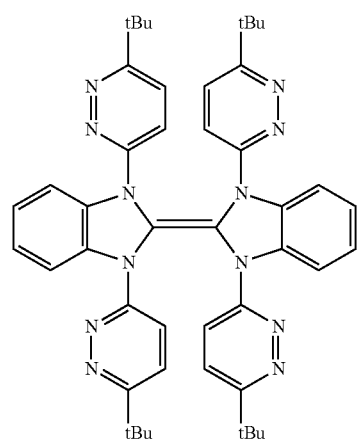
B11
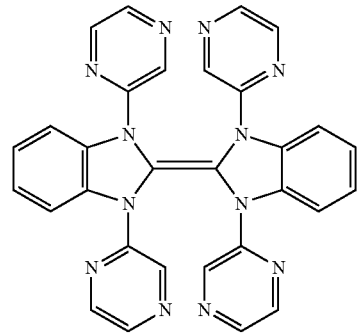
B12
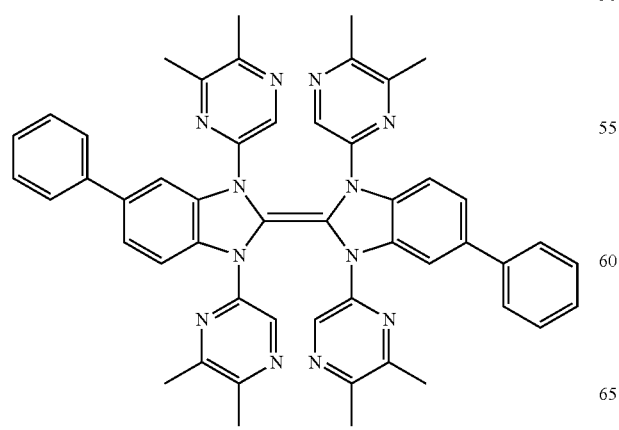
-continued
B13
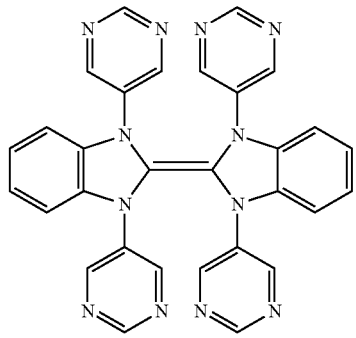
B14
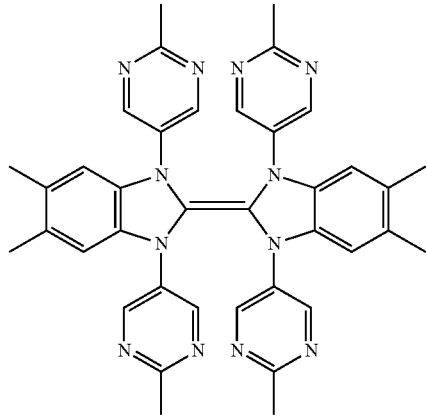
B15
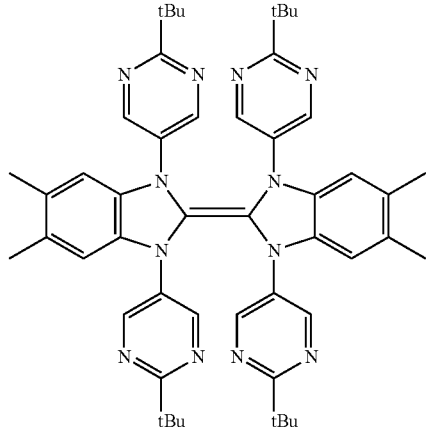
B16
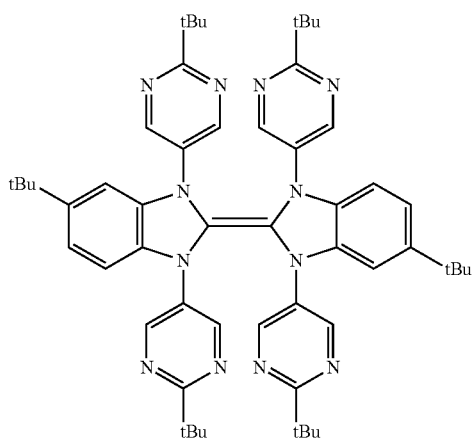

B17 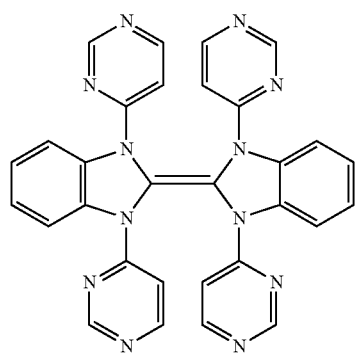
B18 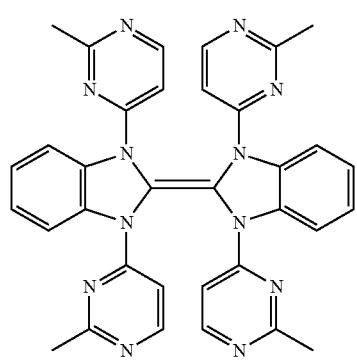
B19 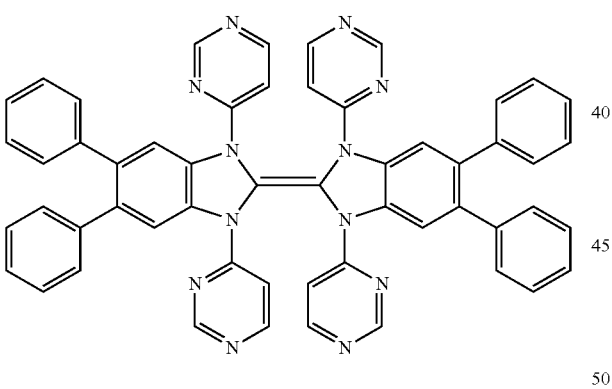
B20 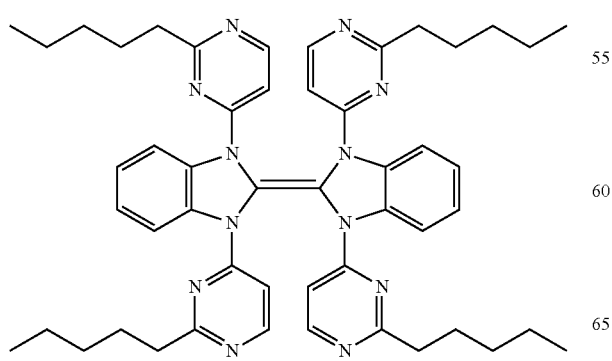
C1 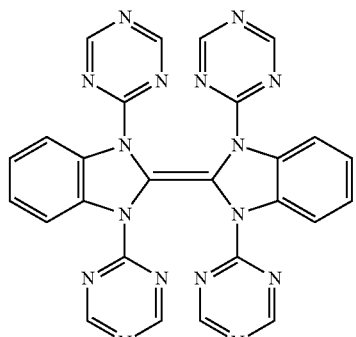
C2 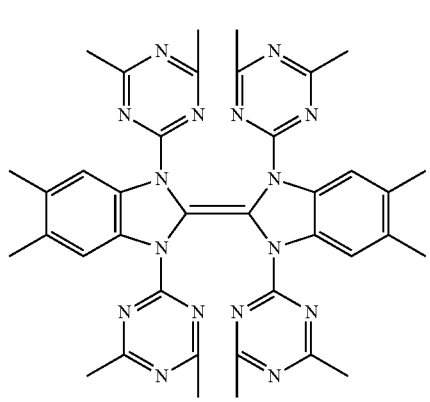
C3 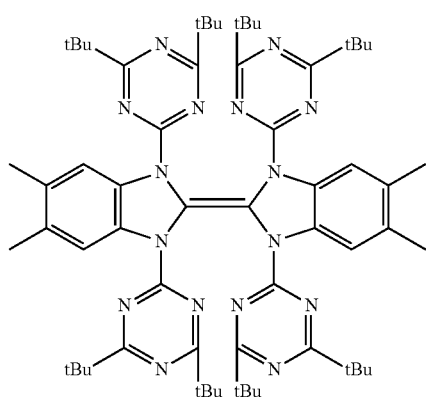
C4 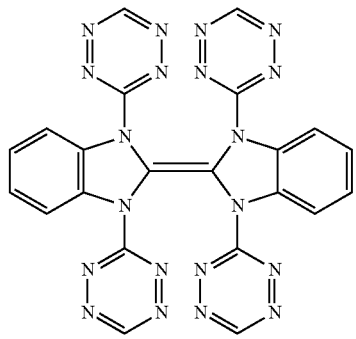

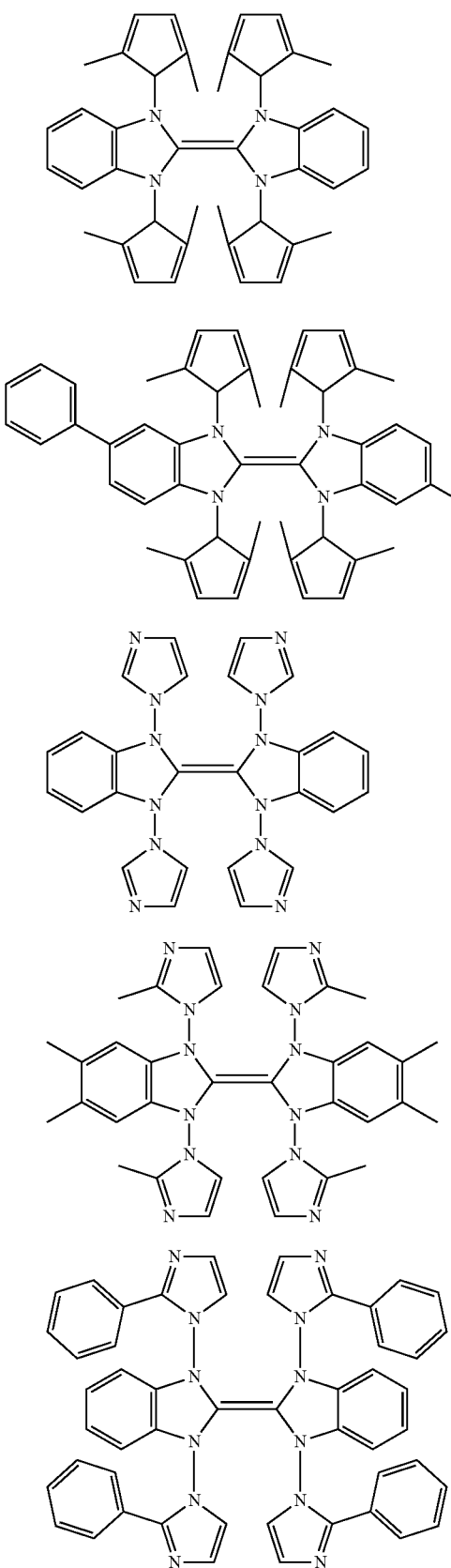
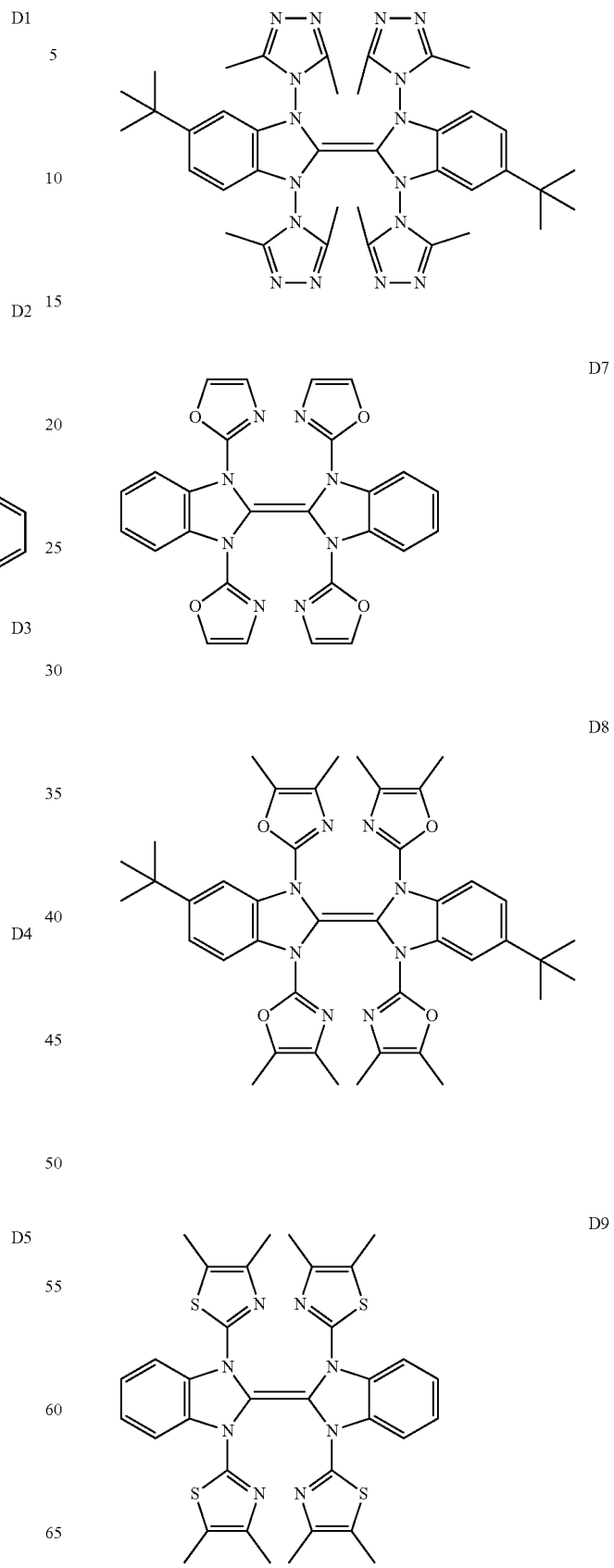

D10
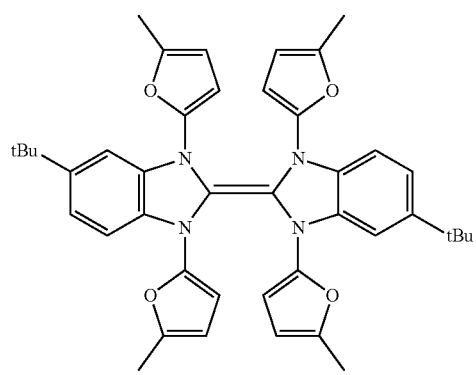
D11
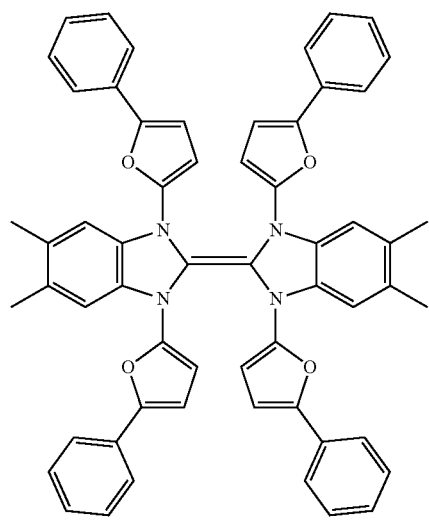
D12
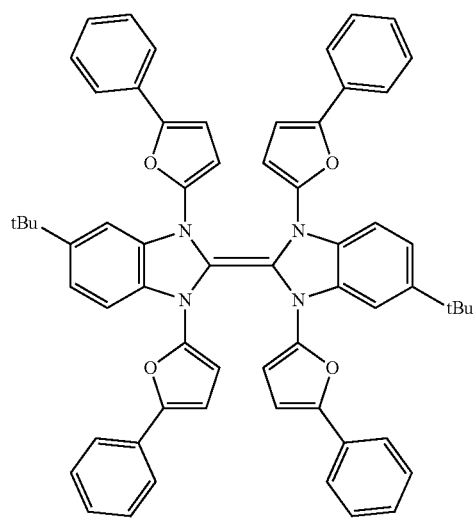
D13
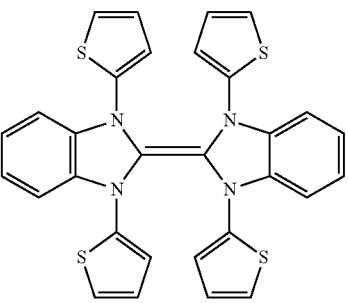
D14
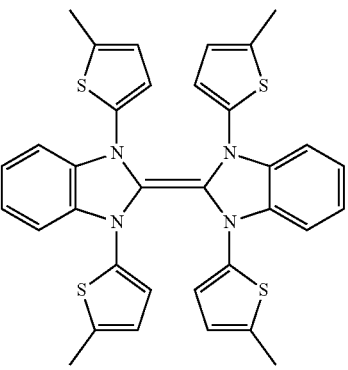
D15
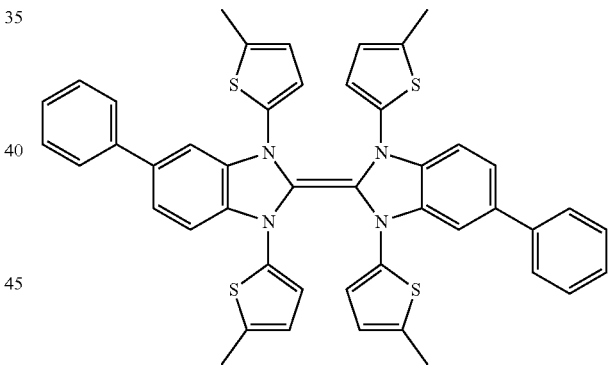
D16
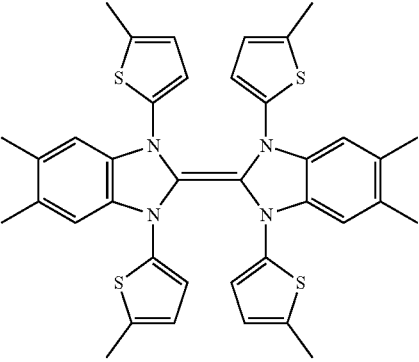

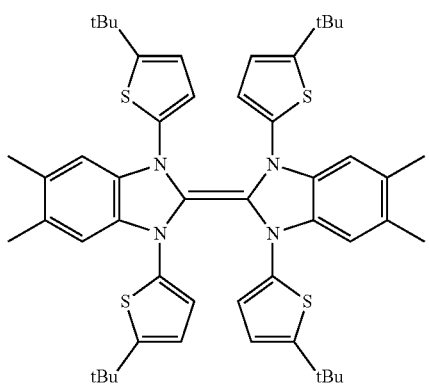

D17

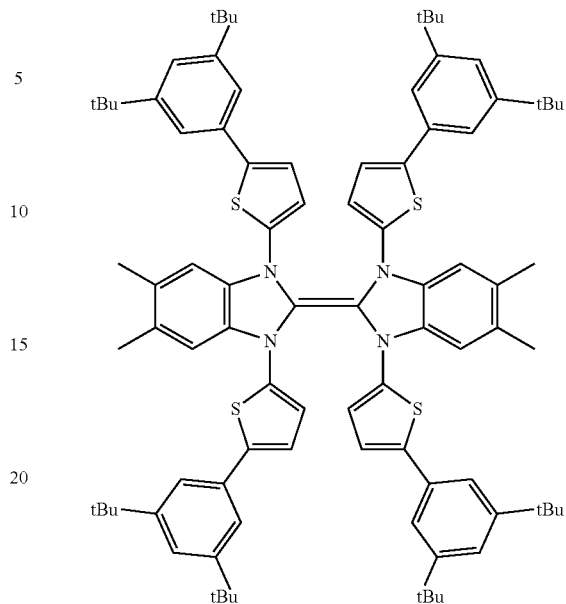

D20

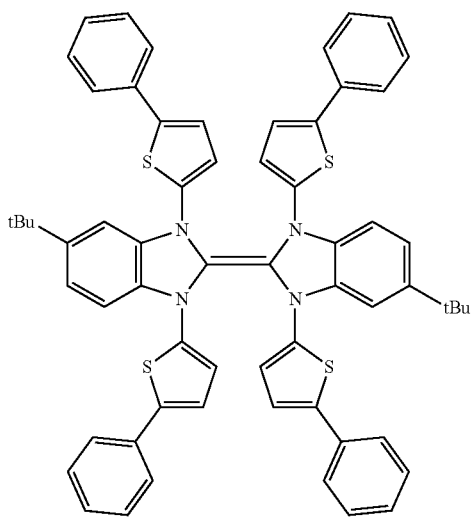

D18

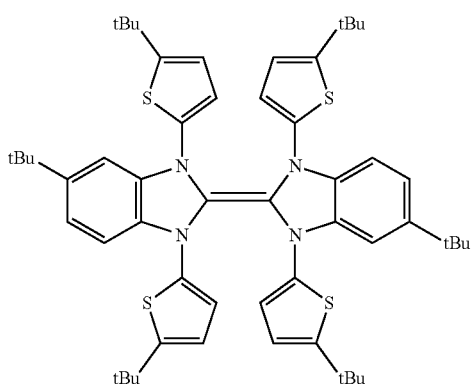

D19

In group A, the heteromonocyclic groups of the exemplified compounds are each 6-membered heteromonocyclic group including a single nitrogen atom. The difference in oxidation potential of these compounds from the 1,1',3,3'-tetrahydro-2,2'-bibenzo[d]imidazolidene skeleton is about 1 V. Thus these compounds have oxidation potentials suitable for carrier injection. In addition, the nitrogen atoms increase the polarity. Consequently, interaction between the organic compound with the electrode and other molecules, and thus the organic compound exhibits good properties.

In other words, the exemplified compounds in Group A each hold a balance between stability and injectability because of the presence of substituted or unsubstituted 2-pyridyl, 3-pyridyl, or 4-pyridyl groups as the heteromonocyclic groups represented by $Ar_1$ to $Ar_4$ in General Formula (1).

In group B, the heteromonocyclic substituents of the exemplified compounds are each 6-membered heteromonocyclic group including two nitrogen atoms. The oxidation potential of these exemplified compounds vary more than the exemplified compounds of Group A, and the number of unpaired electrons is increased. Accordingly, intermolecular interaction increases.

In other words, the exemplified compounds in group B are organic compounds highly interactive with the electrode and surrounding materials because of the presence of 6-membered heteromonocyclic substituents including two nitrogen atoms represented by $Ar_1$ to $Ar_4$ in general formula (1).

In group C, the heteromonocyclic substituents of the exemplified compounds are each 6-membered heteromonocyclic group including three or more nitrogen atoms. These compounds have more unpaired electrons than the exemplified compounds of Group B and are accordingly more interactive with the electrode and surrounding materials.

In other words, the exemplified compounds in group C are organic compounds more highly interactive with the electrode and surrounding materials because of the presence of 6-membered heteromonocyclic substituents including three or more nitrogen atoms represented by $Ar_1$ to $Ar_4$ in general formula (1).

In group D, the heteromonocyclic substituents of the exemplified compounds are each 5-membered heteromonocyclic group. Since the heteromonocyclic groups are 5-membered rings, the molecular weight of these compounds are smaller. Accordingly, these compounds are more easily sublimated and, the oxidation potential thereof varies much. Also, the presence of unpaired electrons help the intermolecular interaction thereof.

In other words, the exemplified compounds in group D are subliming organic compounds highly interactive with the electrode and surrounding materials because of the presence of 5-membered heteromonocyclic substituents represented by $Ar_1$ to $Ar_4$ in general formula (1).

Synthesis of 2,2'-bibenzo[d]imidazolidene Compound Having heteromonocyclic Groups at the 1-, 1'-, 3- and 3'-Positions A process for synthesizing the present organic compound will now be described. The present organic compound may be synthesized according to the following reaction scheme. In the following reaction scheme, $R_1$ and $R_2$ are substituents to be introduced. To synthesize all the exemplified organic compounds, the 3-bromopyridine skeleton and the 3-aminopyridine skeleton used in the following reaction are replaced with appropriate halogenated heteromonocyclic or aminated heteromonocyclic skeletons, such as a 2-bromopyridine skeleton, a 2-aminoprydine skeleton, a 4-bromopyridine skeleton, a 4-aminopyridine skeleton, a 2-bromopyrimidine skeleton, a 2-aminopyrimidine skeleton, a 2-bromopyrazine skeleton, a 2-aminopyrazine skeleton, a 2-bromopyridazine skeleton, a 2-bromotriazine skeleton, or a 2-bromothiophene skeleton.

[Chem. 10]

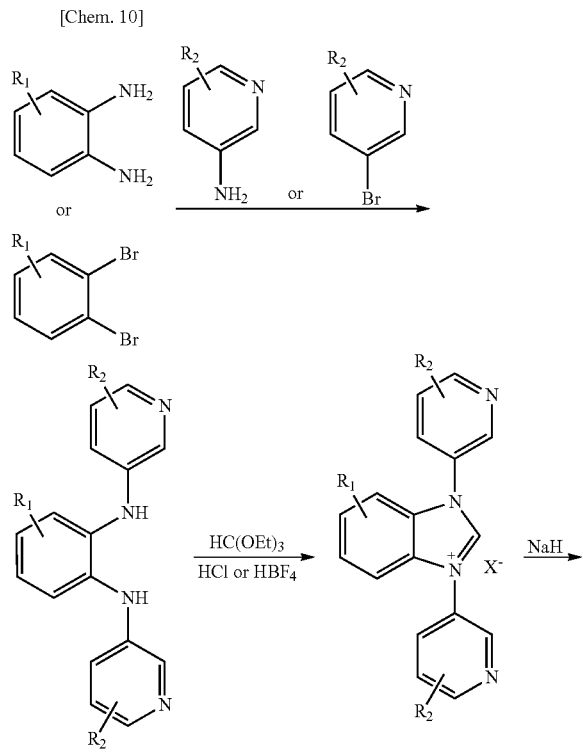

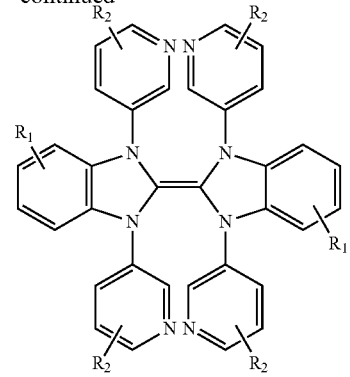

X: Cl or $BF_4$

Organic Electric Field Element

The organic electric field element according to an embodiment of the present invention includes a pair of electrodes, and an organic compound layer disposed between the electrodes. The organic compound layer contains an organic compound expressed by general formula (1).

The organic electric field element of the present embodiment may be an organic light-emitting element, an organic transistor, an organic CMOS sensor, or an organic solar cell.

If the organic electric field element is an organic transistor, the pair of electrodes refers to a set of electrodes. The set of electrodes includes a source, a drain, and a gate electrode. In this instance, the organic compound layer defines an active region of the transistor.

If the organic electric field element is a CMOS sensor or an organic solar cell, the organic compound layer acts as a photoelectric conversion portion. The photoelectric conversion portion receives light to generate electrons. The CMOS sensor includes a pair of electrodes, a photoelectric conversion portion disposed between the electrodes, and a plurality of transistors.

The plurality of transistors include an N-type transistor and a P-type transistor, and the photoelectric conversion portion includes the organic compound layer according to an embodiment of the present invention.

The plurality of transistors are connected to one of the pair of electrodes. The connection between the transistors and the electrode may be established directly or indirectly with another element therebetween. The N-type and p-type transistors may be made of silicon, or may be an organic transistors or contain an oxide semiconductor. The organic CMOS sensor may include a microlens and a color filter.

The organic compound layer may be composed of a single layer or a plurality of layers. The organic compound expressed by general formula (1) may be used in any layer of the organic compound layers.

The organic light-emitting element according to an embodiment of the present invention includes an anode and a cathode, and a luminescent layer disposed between the anode and the cathode, and further includes an organic compound layer between the cathode and the luminescent layer. The organic compound layer contains the organic compound expressed by general formula (1).

The organic light-emitting element may include a hole injection layer, a hole transport layer, an electron blocking layer, a hole blocking layer, an electron transport layer, an electron injection layer, and other layers as the organic compound layer included in addition to the luminescent layer. The luminescent layer may be composed of a single layer or a plurality of layers.

In the organic light-emitting element of the present embodiment, at least one layer disposed between the cathode and the luminescent layer contains the present organic compound.

More specifically, any of the luminescent layer, the hole blocking layer, the electron transport layer, the electron injection layer, and the like contains the present organic compound. Advantageously, the present organic compound is contained mainly in at least one of the electron injection layer and the electron transport layer, desirably in the electron injection layer.

In the present embodiment, the organic compound layer disposed between the cathode and the luminescent layer is referred to as the electron transport layer and/or the electron injection layer, and the organic compound layer in contact with the cathode is referred to as the electron injection layer.

Although the present organic compound may be used solely, it is advantageous to be used as a mixture with another compound (hereinafter referred to as the additional compound).

In this instance, the proportion of the additional compound may be in the range of more than 0% by weight to 80% by weight, relative to the total weight of this additional compound and the present organic compound. In the case, for example, where an electron transport layer and an electron injection layer are disposed between the cathode and the luminescent layer, the organic compound in the electron transport layer is not taken into account for the calculation of this proportion.

The proportion of the additional compound can be estimated by subjecting the organic compound layer containing the present organic compound to TOF-SIMS analysis or the like. Alternatively, the organic compound extracted from the organic light-emitting element may be measured with IR or UV or by NMR.

The additional compound desirably has a higher oxidation potential than the present organic compound.

Desirably, the additional compound may be an anthraquinone derivative, a fluorene derivative, a naphthalene derivative, an indene derivative, a terphenyl derivative, an acenaphthofluoranthene derivative, an indenoperylene derivative, or a phenanthroline derivative.

The organic light-emitting element may have any one of the following multilayer structure including one or more organic compound layers on a substrate.

(1) anode/luminescent layer/cathode
(2) anode/hole transport layer/luminescent layer/electron transport layer/cathode
(3) anode/hole transport layer/luminescent layer/electron transport layer/electron injection layer/cathode
(4) anode/hole injection layer/hole transport layer/luminescent layer/electron transport layer/cathode
(5) anode/hole injection layer/hole transport layer/luminescent layer/electron transport layer/electron injection layer/cathode
(6) anode/hole transport layer/electron blocking layer/luminescent layer/hole blocking layer/electron transport layer/cathode These are merely basic structures and are not intended to limit the structure of the organic light-emitting element containing the present organic compound.

The organic light-emitting element may take various structures. For example, the organic light-emitting element of an embodiment may further include an insulating layer between an electrode and an organic compound layer, or may have an adhesion layer or an interference layer. The electron transport layer or the hole transport layer may be composed of two layers having different ionization potentials, or the luminescent layer may be composed of two layers containing different luminescent materials.

The light-emitting element may be of a bottom emission type that emits light through the substrate, of a top emission type that emits light through the opposite side to the substrate, or of a type that emits light through both sides.

Among the above structures, structure (6) including both an electron blocking layer and a hole blocking layer is advantageous. Structure (6) enables holes and electrons to be confined in the luminescent layer without leaking the carriers, thus achieving an organic light-emitting element having high emission efficiency.

The luminescent layer of the organic light-emitting element of an embodiment may contain a plurality of constituents including a main constituent and sub constituents. The main constituent refers to the compound accounting for the highest percentage, on a weight basis, of the constituents in the luminescent layer, and may be referred to as the host material. The host material is a compound present around the molecules of a guest material as the matrix of the luminescent layer, and functions mainly to transport carriers and supply excitation energy to the guest material.

The sub constituents are compounds other than the main constituent. Sub constituents include a guest material, a luminescence assist material, and a charge injection material. The guest material may be called a dopant material. The luminescence assist material and the charge injection material may have the same structure or different structures. These compounds are sub constituents, but may be called host material 2 to distinguish from the guest material. The guest material in the luminescent layer is a compound that functions for the major light emission.

The guest material content is in the range of 0.01% by weight to less than 50% by weight, preferably in the range of 0.1% by weight to 20% by weight, relative to the total weight of the compounds constituting the luminescent layer. Desirably, the guest material content is 10% by weight or less from the viewpoint of preventing concentration quenching. The guest material may be present uniformly throughout the layer made of the host material, or may be present with a concentration gradient. Alternatively, the layer of the host material may partially contain the guest material so as to have a portion not containing the guest material.

The luminescent layer may be composed of a single layer, or a plurality of luminescent layers may be used. Also, two or more luminescent materials emitting different colors may be used for mixing colors. If a plurality of luminescent layers are used, the luminescent layers may form a multilayer structure or may be arranged in a lateral manner. In the case of the arrangement in a lateral manner, all the luminescent layers are in contact with the carrier transport layer. In this instance, the organic light-emitting element may emit, but is not limited to, color light from blue to green or red.

For example, the emission color may be white or intermediate color. For emitting white light, the luminescent layers each emit red, blue, or green. The luminescent layer may be formed by vapor deposition or coating.

In an embodiment, the luminescent layer of the organic light-emitting element may contain a plurality of luminescent materials. Any two materials of the plurality of luminescent materials may emit different light rays from each other, and a light-emitting element including such a luminescent layer may define an element capable of emitting white light.

Alternatively, the organic light-emitting element may include a plurality of luminescent layers, and at least one of the plurality of luminescent layers may emit light having a different wavelength from other luminescent layers. The colors of light from these luminescent layers may be mixed so that the organic light-emitting element can emit white light.

In the present embodiment, the hole blocking layer refers to a layer that blocks holes, and is disposed adjacent to the side of the luminescent layer closer to the cathode.

The present organic compound may be used in combination with a luminescent material of a low-molecular-weight compound or a polymer, a hole-injecting compound, a hole-transporting compound, a compound that can act as a host, a luminescent compound, an electron-injecting compound, or an electron-transporting compound, if necessary.

These compounds will now be described.

The hole-injecting or transporting material desirably has so high a hole mobility as facilitates hole injection from the anode and enables the injected holes to be transported to the luminescent layer. From the viewpoint of preventing the crystallization or any other deterioration of the material in the organic light-emitting element, the hole-injecting or transporting material desirably has a high glass transition temperature. Low-molecular-weight or polymeric hole-injecting or transporting materials include triarylamine derivatives, arylcarbazole derivatives, phenylenediamine derivatives, stilbene derivatives, phthalocyanine derivatives, porphyrin derivatives, poly(vinyl carbazole), polythiophene, and other conductive polymers. The hole-injecting or transporting material is also used suitably in the electron blocking layer.

Exemplary compounds that can be used as the hole-injecting or transporting material include, but are not limited to, the following.

[Chem. 11]

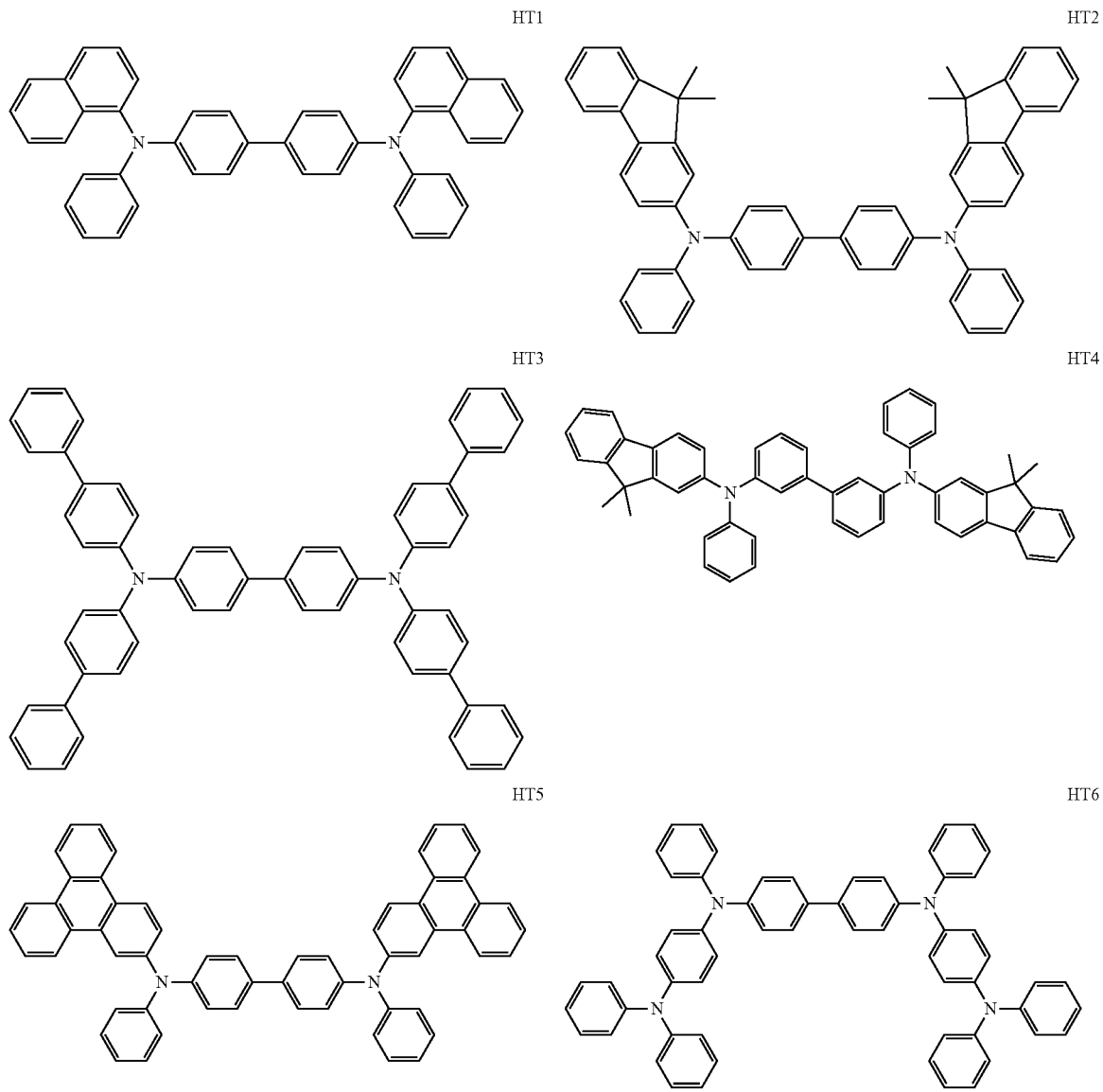

-continued
HT7
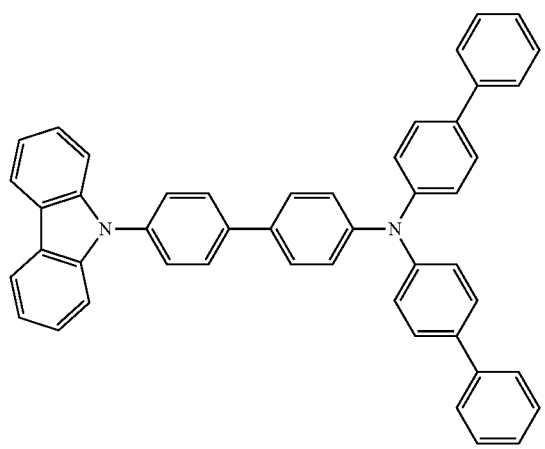
HT8
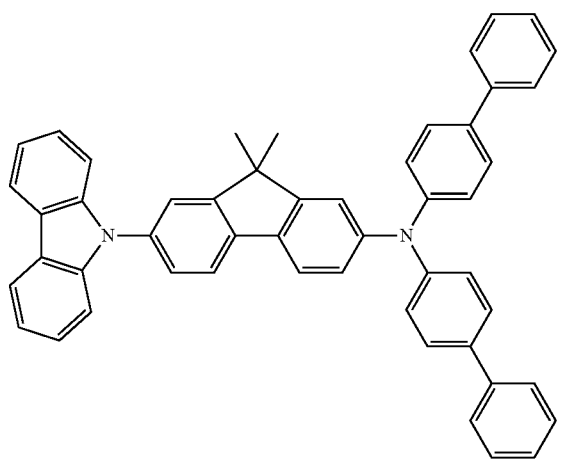
HT9
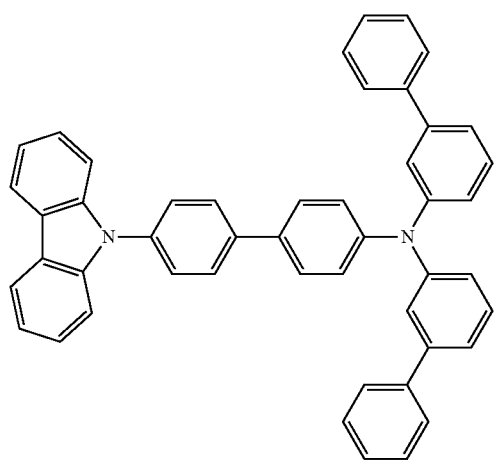
HT10
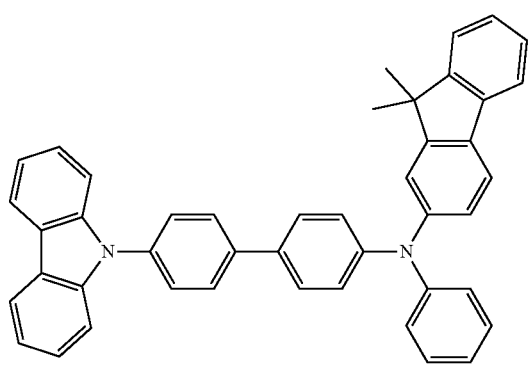
HT11
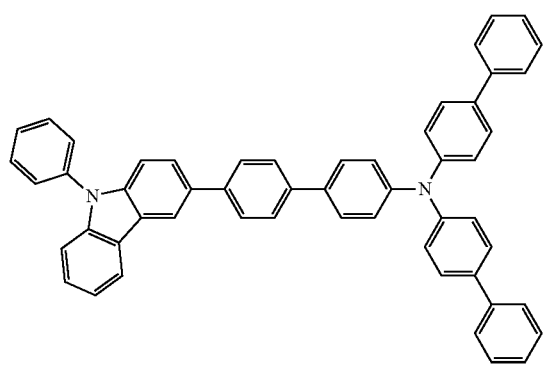
HT12
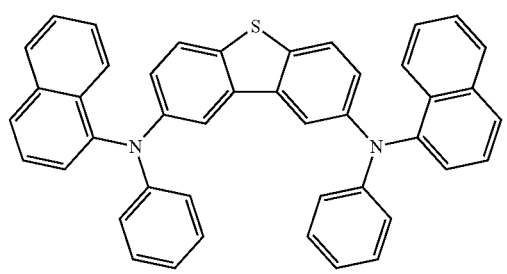

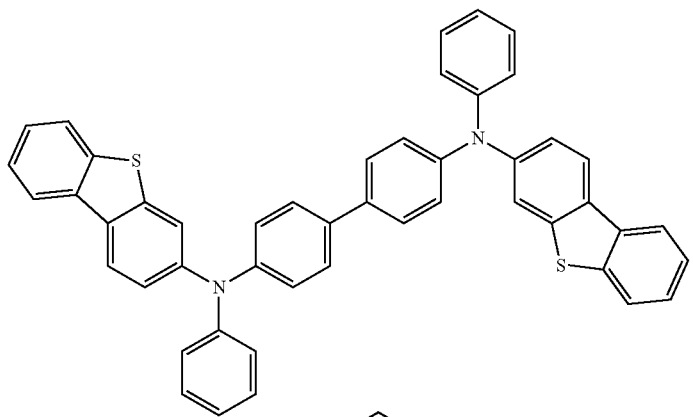

HT13

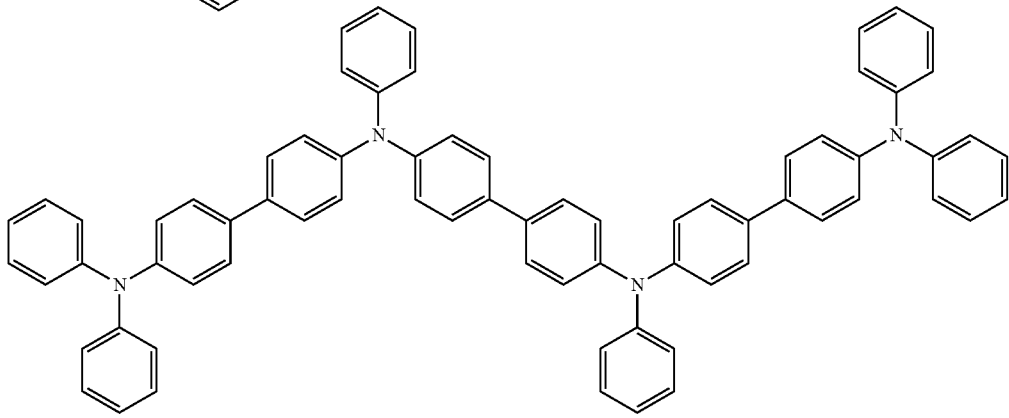

HT14

Luminescent materials involved in light emission include condensed ring compounds (such as fluorene derivatives, naphthalene derivatives, pyrene derivatives, perylene derivatives, tetracene derivatives, anthracene derivatives, and rubrene), quinacridone derivatives, coumarin derivatives, stilbene derivatives, organic aluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, polyfluorene derivatives, and polyphenylene derivatives.

Exemplary compounds that can be used as the luminescent material include, but are not limited to, the following.

[Chem. 12]

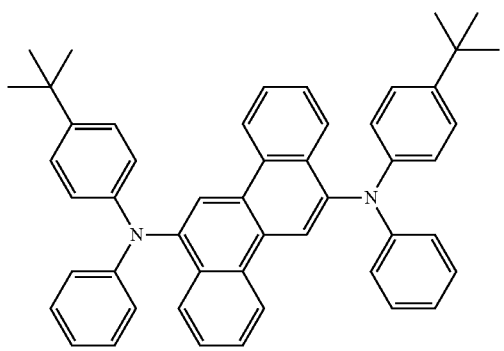

BD1

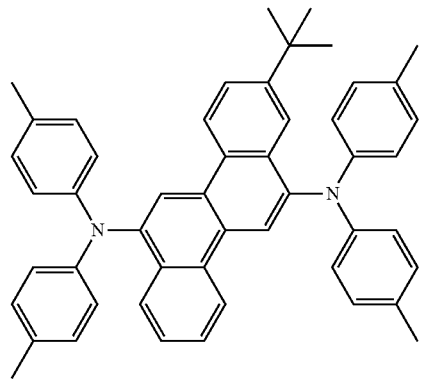

BD2

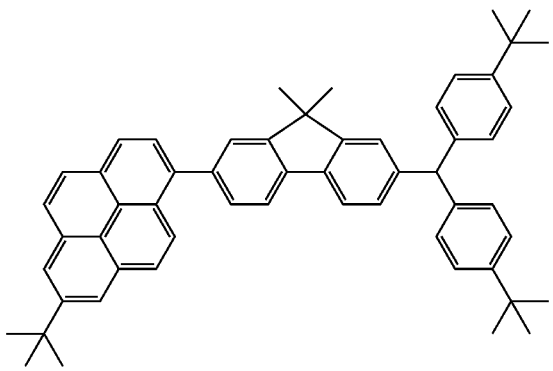

BD3

BD4
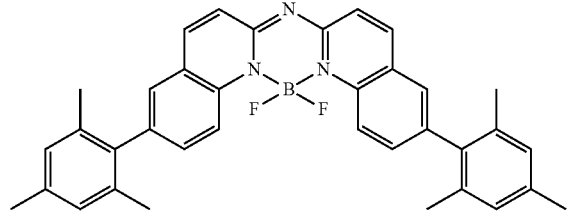
BD5
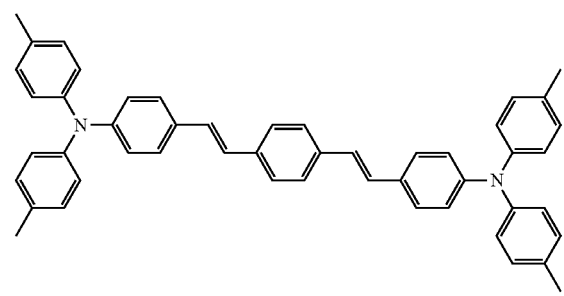
BD6
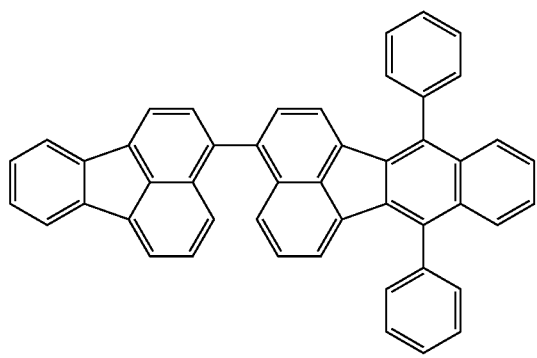
BD7
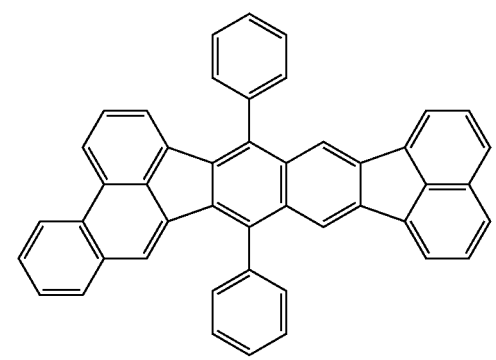
BD8
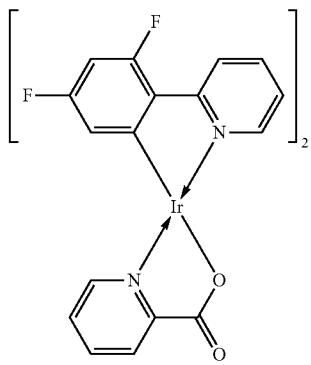
GD1
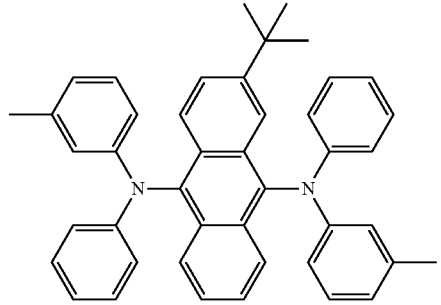
GD2
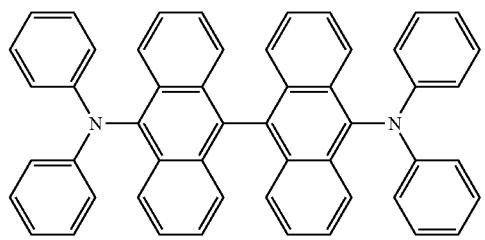
GD3
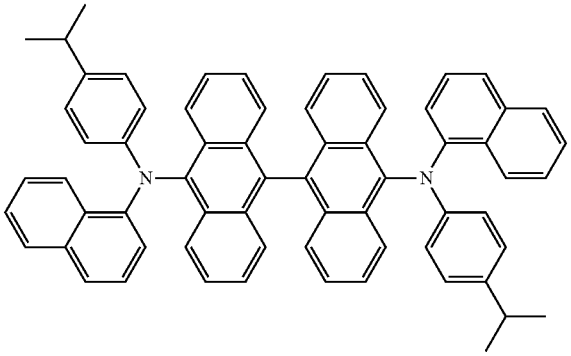
GD4
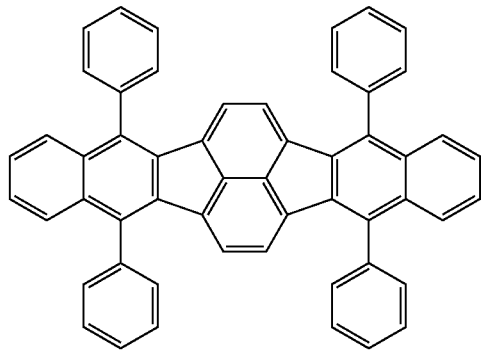

GD5 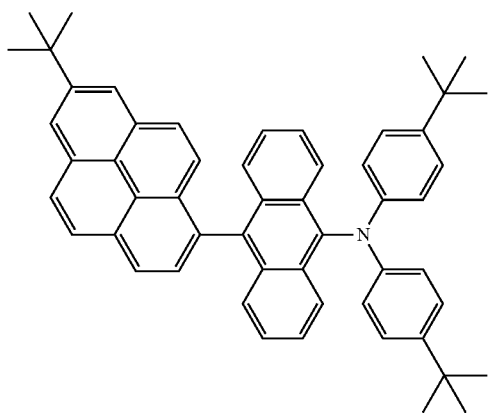
GD6 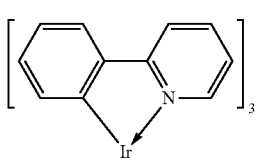
GD7 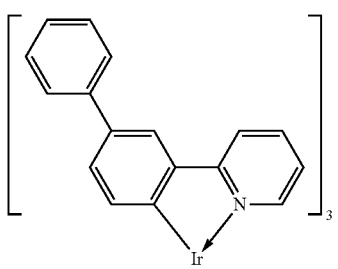
GD8 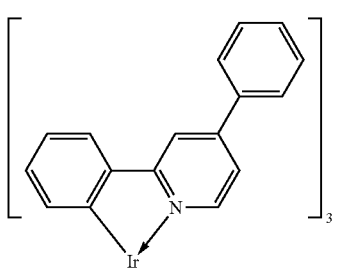
RD1 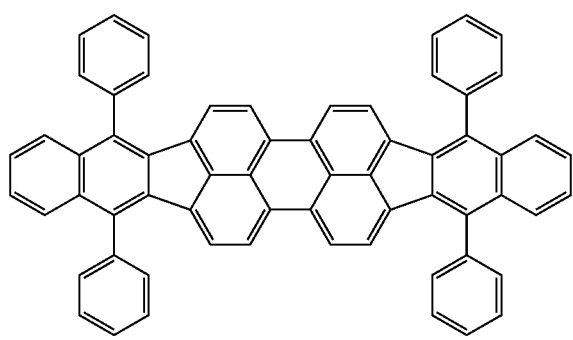
RD2 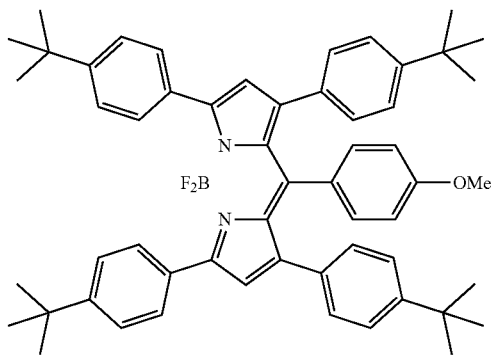
RD3 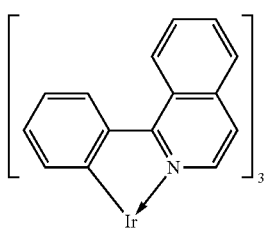
RD4 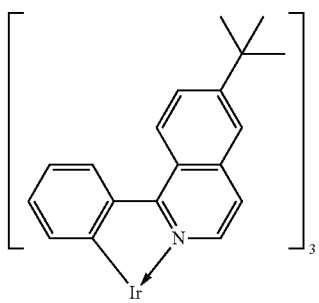
RD5 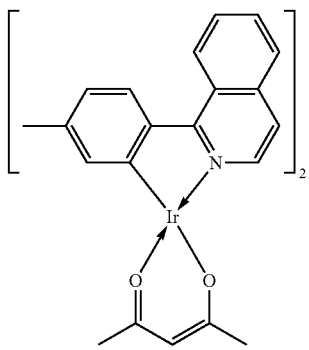

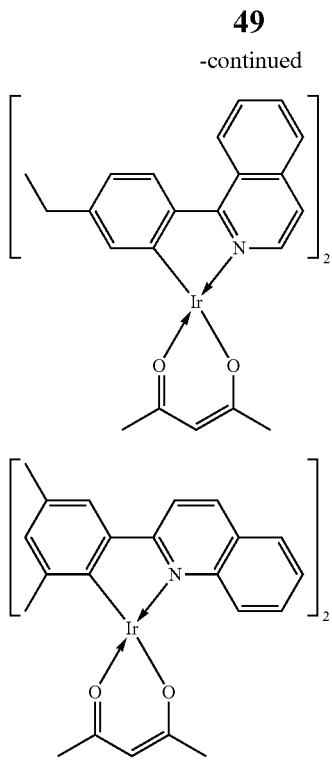

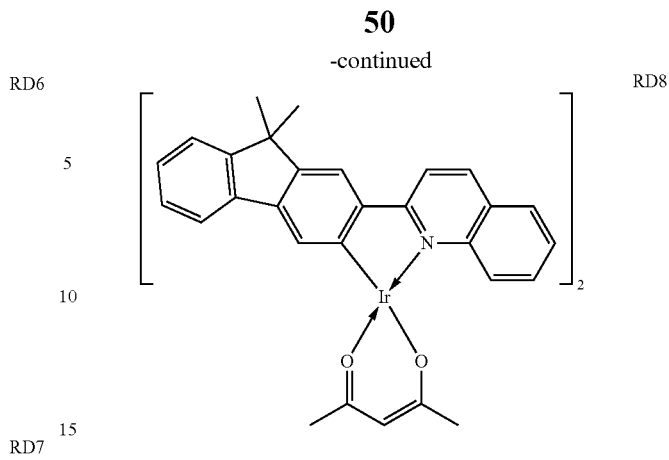

Host or luminescence assist materials that can be used in the luminescent layer include aromatic hydrocarbons and derivatives thereof, carbazole derivatives, dibenzofuran derivatives, dibenzothiophene derivatives, organic aluminum complexes such as tris(8-quinolinolato) aluminum, and organic beryllium complexes.

Exemplary compounds that can be used as the host or luminescent assist material include, but are not limited to, the following.

[Chem. 13]

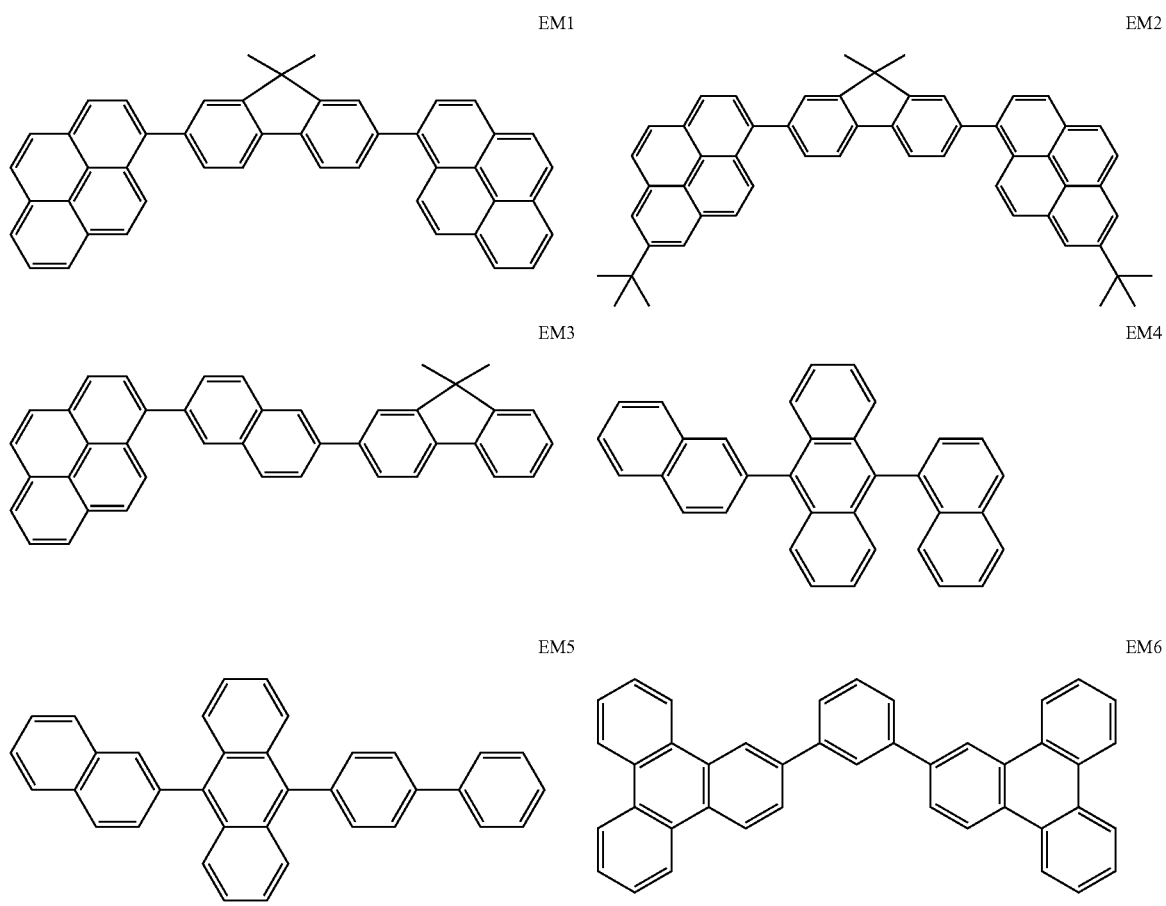

-continued
EM7
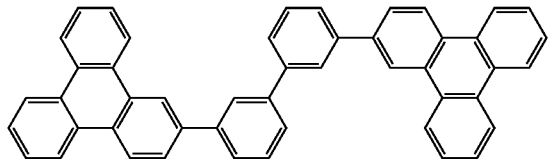
EM8
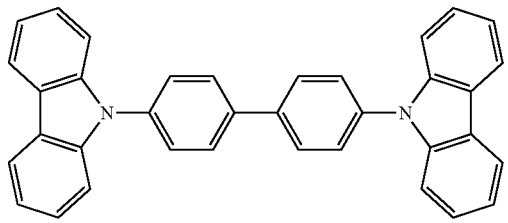
EM9
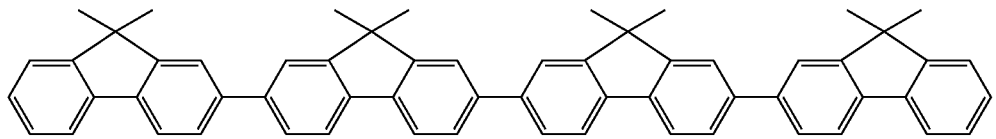
EM10
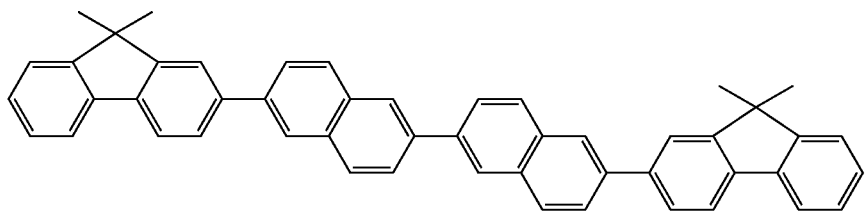
EM12
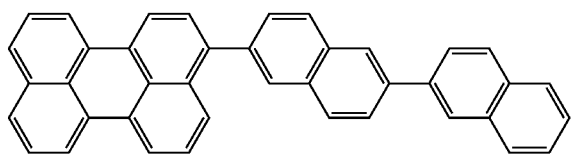
EM11
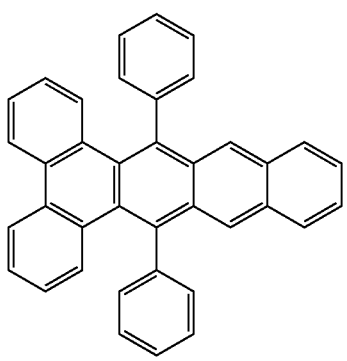
EM13
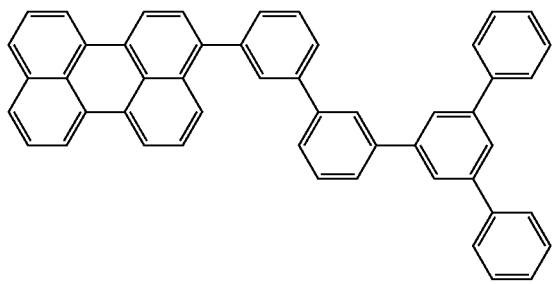
EM14
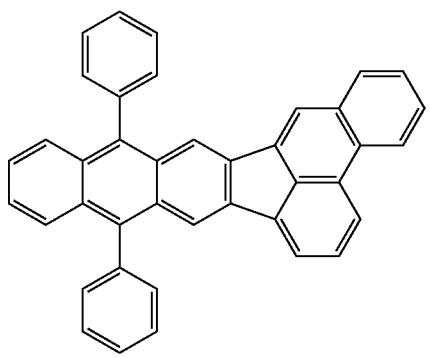
EM15
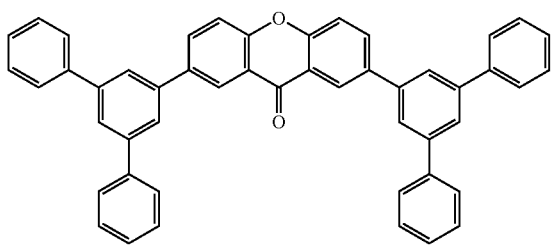
EM16
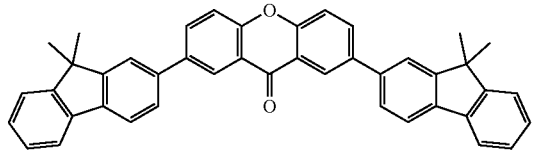

EM17

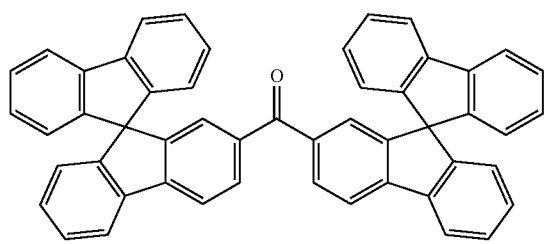

The electron-transporting material can be selected from the compounds capable of transporting electrons injected from the cathode to the luminescent layer in view of the balance with the hole mobility of the hole-transporting material. Electron-transporting materials include oxadiazole derivatives, oxazole derivatives, pyrazine derivatives, triazole derivatives, triazine derivatives, quinoline derivatives, quinoxaline derivatives, phenanthroline derivatives, organic aluminum complexes, and condensed ring compounds (such as fluorene derivatives, naphthalene derivatives, chrysene derivatives, and anthracene derivatives). These electron-transporting materials are also used suitably in the hole blocking layer.

Exemplary compounds that can be used as the electron-transporting material include, but are not limited to, the following.

[Chem. 14]

ET1

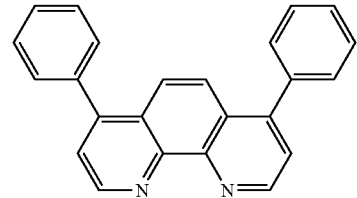

ET2

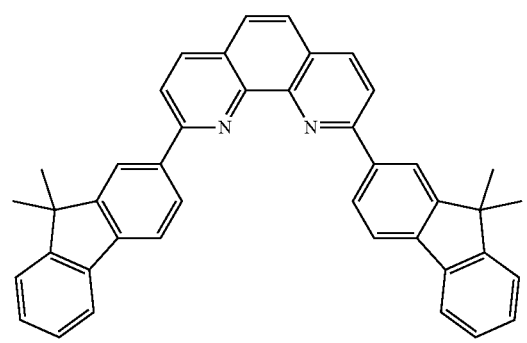

ET3

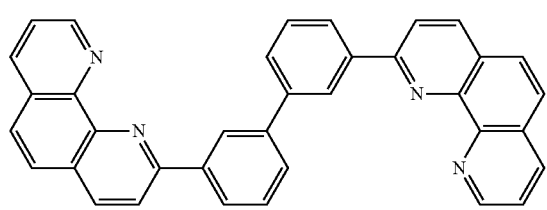

ET4

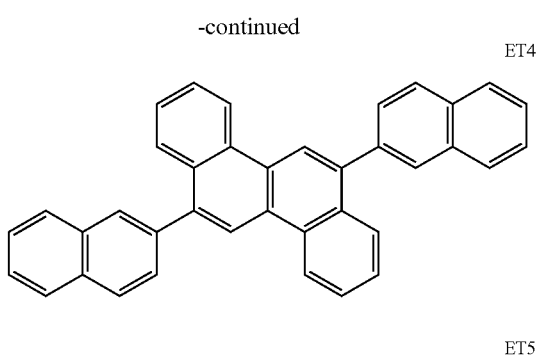

ET5

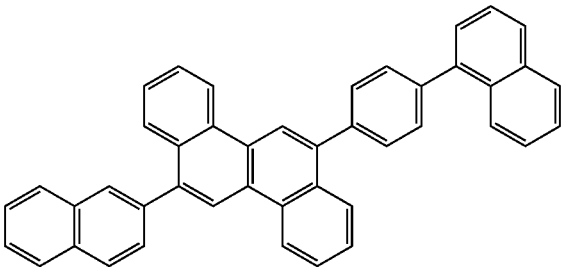

ET6

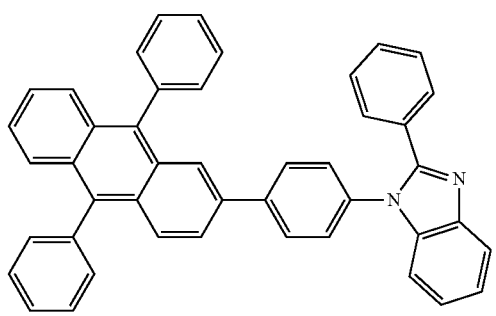

ET7

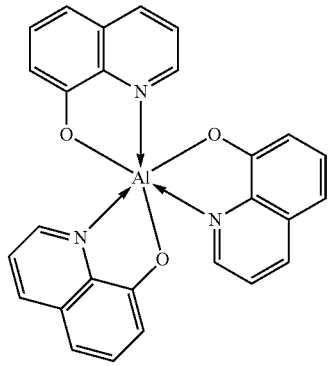

ET8

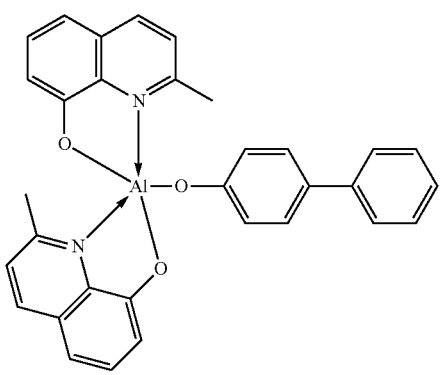

[Chem. 15]

EI1

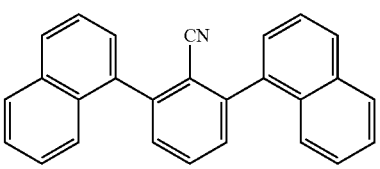

EI2

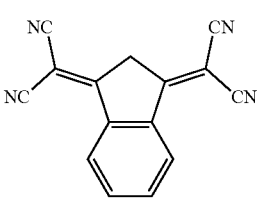

ET9

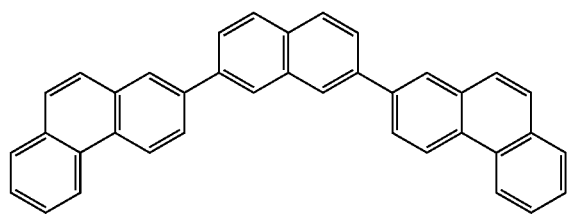

EI3

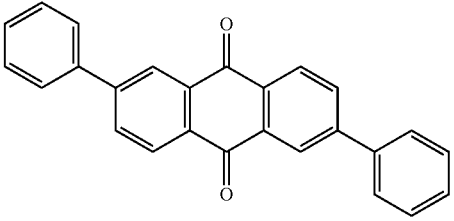

ET10

EI4

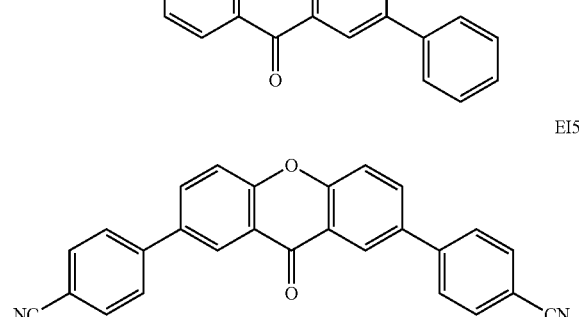

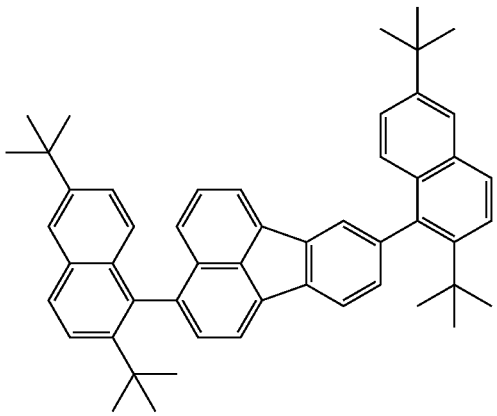

EI5

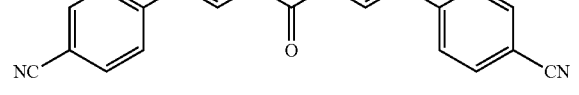

EI6

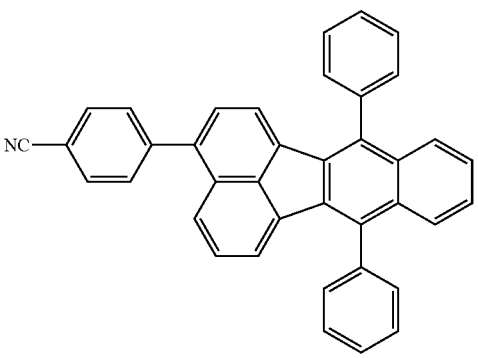

The electron-injecting material may be selected from the compounds that can facilitate the injection of electrons from the cathode in view of the balance with hole injectability. The present 2,2'-bibenzo[d]imidazolidene compound having heteromonocyclic groups at the 1-, 1'-, 3- and 3'-positions may be mixed with an electron-transporting material.

The present organic compound may be used as a mixture with the following materials having a cyano group, a fluorine atom, a fluoranthene skeleton, or a condensed ring. The material having a fluoranthene skeleton refers to a compound having a fluoranthene structure in the chemical structure of the molecule thereof. Among the cited compounds, ET10, EI6, EI7, EI8, EI9, EI12, EI14, EI15, EI16, EI17, EI18 and EI19 are compounds having a fluoranthene structure.

EI7
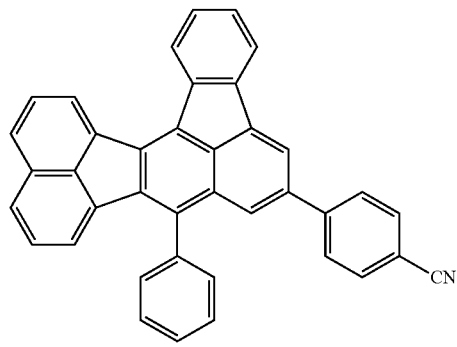
EI12
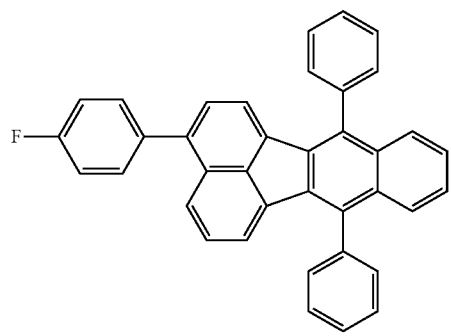
EI8
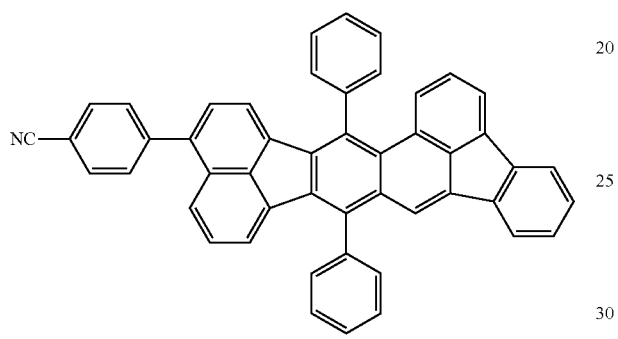
EI13
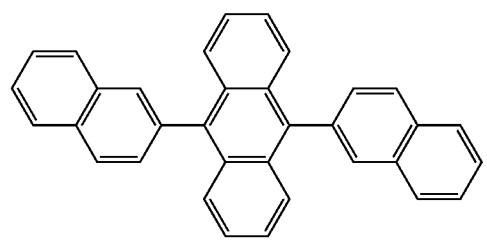
EI9
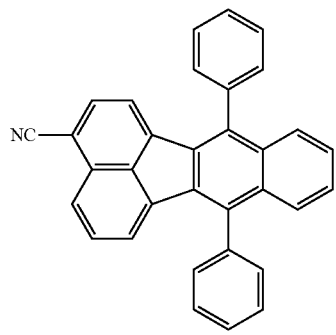
EI14
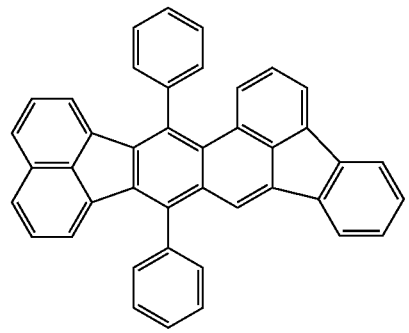
EI10
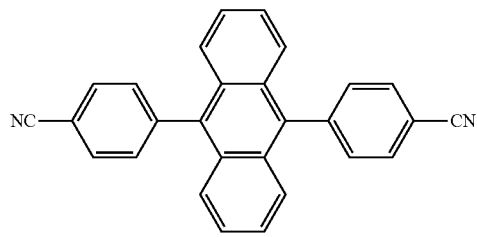
EI15
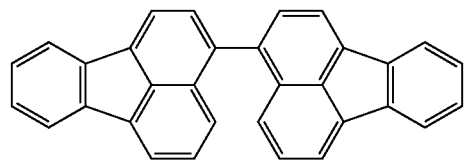
EI11
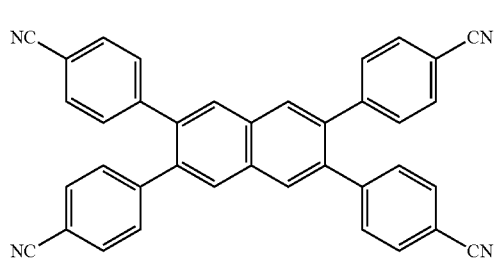
EI16
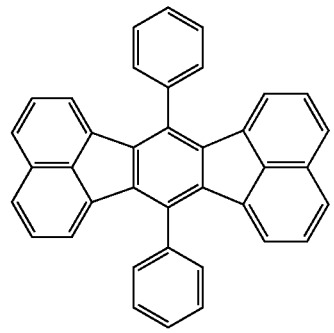

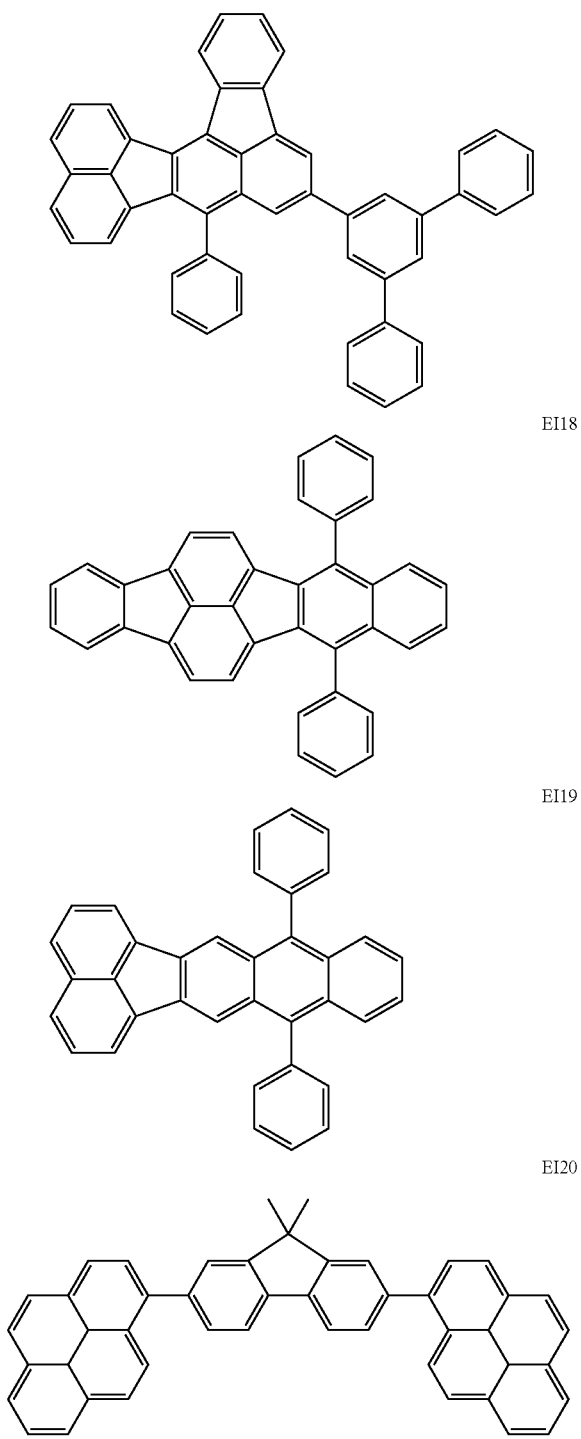

The anode is desirably made of a compound having as high a work function as possible. Such materials include simple metals, such as gold, platinum, silver, copper, nickel, palladium, cobalt, selenium, vanadium, and tungsten, and mixtures therewith or alloys thereof; and metal oxides, such as tin oxide, zinc oxide, indium oxide, indium tin oxide (ITO), and zinc indium oxide. Electrically conductive materials can also be used, such as polyaniline, polypyrrole, and polythiophene.

These electrode materials may be used singly or in combination. The anode may be composed of a single layer or a plurality of layers.

The cathode is desirably made of a compound having a low work function. Examples of the cathode material include alkali metals, such as lithium; alkaline-earth metals, such as calcium; other simple metals such as aluminum, titanium, manganese, silver, lead, and chromium; and mixtures of these simple metals. Alloys of these simple metals may be used. Examples of such an alloy include magnesium-silver, aluminum-lithium, aluminum-magnesium, silver-copper, and zinc-silver. A metal oxide, such as indium tin oxide (ITO), may be used. These electrode materials may be used singly or in combination. The cathode may be composed of a single layer or a plurality of layers.

The organic compound layers (hole injection layer, hole transport layer, electron blocking layer, luminescent layer, hole blocking layer, electron transport layer, electron injection layer, etc.) of the organic light-emitting element of the present embodiment may be formed by the following process.

The organic compound layers of the organic light-emitting element may be formed in a dry process performed by, for example, vacuum deposition, ionized deposition, sputtering, or using plasma. Alternatively, the organic compound layers may be formed in a wet process performed by a known coating method using a material dissolved in a solvent, such as spin coating, dipping, a cast method, Langmuir-Blodgett (LB) method, or an ink jet method.

Layers formed by vacuum deposition, solution coating or the like are unlikely to crystallize and are thus superior in stability with time. For the coating method, an appropriate binder resin may be used in combination.

Examples of the binder resin include, but are not limited to, polyvinylcarbazole resin, polycarbonate resin, polyester resin, ABS resin, acrylic resin, polyimide resin, phenol resin, epoxy resin, silicone resin, and urea resin.

These binder resins may be used in the form of homopolymer or copolymer as a single material, or may be used in combination in the form of mixture. Other known additives, such as a plasticizer, an antioxidant, and an ultraviolet light adsorbent, may further be used, if necessary.

Applications of Organic Light-Emitting Element

The organic light-emitting element of the present embodiment can be used for a display device or a lighting device. In addition, the organic light-emitting element may be used as an exposure light source of an electrophotographic image forming apparatus, a back light of a liquid crystal display device, or a light-emitting device including a white light source provided with a color filter. The color filter may transmit at least one of three colors: red, green, and blue.

The display device according to an embodiment includes a plurality of pixels, and at least one of the pixels includes the organic light-emitting element according to the present embodiment. This pixel includes the organic light-emitting element of the present embodiment and an active element. The active element may be a switching element or an amplifier element. More specifically, the active element may be a transistor. Either the anode or the cathode of the organic light-emitting element is electrically connected to either the drain or the source electrode of the transistor. The transistor may contain an oxide semiconductor in the active region thereof. The oxide semiconductor may be amorphous or crystalline, or may contain amorphous phases and crystalline phases. The crystals may be monocrystalline or microcrystalline, or specific axes thereof, such as the C-axes, may be aligned. The crystals in two or more of these states may be mixed.

An organic light-emitting device including such a switching element may be used as an image display device in which organic light-emitting elements act as pixels, or may be used as a lighting device. Alternatively, the organic light-emitting device may be used as an exposure light source of an electrophotographic image forming apparatus, such as a laser beam printer or a copy machine.

The display device may be used as an image display device of a PC or the like. The transistor may be a thin film transistor (TFT) element. The TFT element may be formed on the insulating surface of a substrate. The TFT element controls the luminance of emitted light.

Alternatively, the display device may be used in an image information processing apparatus that includes an input portion to which image information is input from an area CCD, a linear CCD, a memory card, or the like and an information processing portion adapted to process the inputted information, and that thus displays the inputted information on a display portion.

The display portion of an image sensing device or an ink jet printer may have a function as a touch panel. The touch panel function may be operated by, but not limited to, a scheme using infrared, capacitance, resistive film, or electromagnetic induction.

Also, the display device may be used as a display portion of a multifunction printer.

The lighting device illuminates, for example, a room. The lighting device may emit white light (having a color temperature of 4200 K), neutral white light (having a color temperature of 5000 K), or any other color light from blue to red. At least any one of the organic light-emitting elements in the lighting device is the organic light-emitting element of an embodiment of the present invention.

The lighting device according to an embodiment includes the organic light-emitting element of the present embodiment and an AC/DC converter connected to the organic light-emitting element. The AC/DC converter converts alternating voltage into direct voltage. This converter is a circuit adapted to supply a driving voltage to the organic light-emitting element. The lighting device may further include a color filter.

The lighting device may include a heat radiation portion. The heat radiation portion is intended to dissipate heat from the device and may be made of, for example, a metal having a high specific heat or liquid silicon.

The image forming apparatus according to an embodiment of the present invention includes a photosensitive member, an exposure portion that exposes the photosensitive member, a charging member that charges the photosensitive member, and a developing portion that applies a developer to the photosensitive member. In the image forming apparatus, the exposure portion includes a plurality of organic light-emitting elements of the present embodiment. The developer may be a toner or an ink. The toner may be dry or liquid.

The organic light-emitting element of the present embodiment can be used as a member of an exposure device adapted to expose the photosensitive member. The exposure device according to an embodiment of the present invention has a plurality of emission points or the like, and at least one of the emission points includes the organic light-emitting element of the present embodiment. The emission points are arranged in a line along the longitudinal direction of the photosensitive member.

Figure 2:
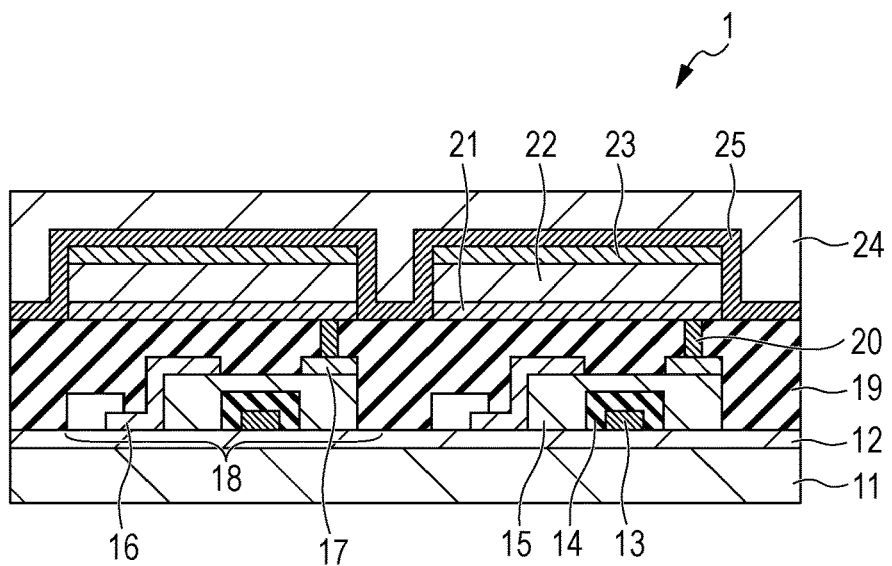
FIG. 2 is a schematic sectional view of a display device including organic light-emitting elements of an embodiment of the present invention and active elements each connected to the corresponding organic light-emitting element.

The display device according to an embodiment of the present invention will now be described with reference to a figure. FIG. 2 is a schematic sectional view of a display device including organic light-emitting elements and TFT elements each connected to the corresponding organic light-emitting element. The TFT elements are a type of active elements.

The display device 1 shown in FIG. 2 includes a substrate 11 made of glass or the like, and a moisture-proof film 12 over the substrate for protecting TFT elements or organic compound layers. Reference numeral 13 designates a metal gate electrode. Reference numeral 14 designates a gate insulating film, and reference numeral 15 designates a semiconductor layer.

Each TFT element 18 includes the semiconductor layer 15, a drain electrode 16, and a source electrode 17. An insulating film 19 is disposed over the TFT elements 18. Each source electrode 17 is connected to the anode 21 of the corresponding organic light-emitting element through a contact hole 20.

The electrical connection from the electrode (anode or cathode) of the organic light-emitting element to the electrode (source electrode or drain electrode) of the TFT is not limited to the manner shown in FIG. 2. In other words, either the anode 21 or the cathode 23 of the organic light-emitting element is electrically connected to either the source electrode 17 or the drain electrode 16 of the TFT element 18.

Although the display device 1 shown in FIG. 2 is illustrated as if it had a single organic compound layer, the organic compound layer 22 may have a plurality of layers. Furthermore, the cathode 23 is provided thereover with a first protective layer 24 for suppressing the degradation of the organic light-emitting element and a second protective layer 25.

Although the display device 1 shown in FIG. 2 includes transistors as switching elements, metal-insulator-metal (MIM) elements may be used as the switching elements instead of the transistors.

Each transistors of the display device 1 shown in FIG. 2 may be a thin film transistor including an active layer on the insulating surface of the substrate without being limited to a transistor formed in a monocrystalline silicon wafer. The active layer of the thin film transistor may be made of a non-monocrystalline silicon, such as monocrystalline silicon, amorphous silicon, or microcrystalline silicon, or a non-monocrystalline oxide semiconductor, such as indium zinc oxide or indium gallium zinc oxide.

The transistors in the display device 1 shown in FIG. 2 may be formed in the substrate, which may be made of Si. To be formed in the substrate implies that the transistors are formed by working the substrate. In other words, a transistor formed in a substrate implies that the substrate and the transistor are formed in one body.

It depends on the definition of the display device whether the transistors are formed in the substrate. For example, for a display device having a definition of a QVGA level for 1 inch, it is advantageous to form transistors in a Si substrate.

Figure 3:
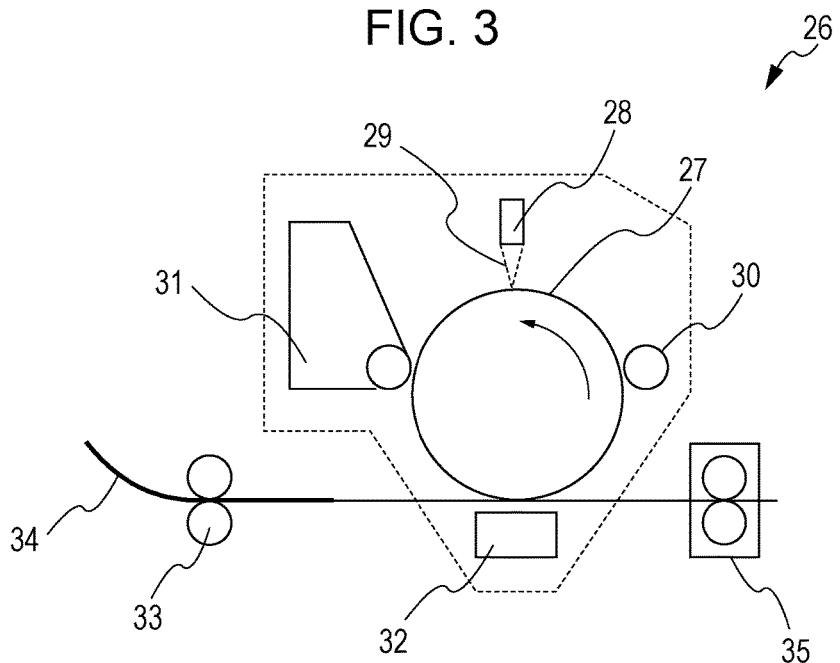
FIG. 3 is a schematic view of an image forming apparatus according to an embodiment of the present invention.

FIG. 3 is a schematic view of an image forming apparatus 26 according to an embodiment of the present invention. The image forming apparatus 26 includes a photosensitive member 27, an exposure light source 28, a developing portion 30, a charging member 31, a transfer device 32, a conveying roller 33, and a fuser 35.

The exposure light source 28 emits light 29 to form an electrostatic latent image on the surface of the photosensitive member 27. The exposure light source 28 includes the organic light-emitting element according to an embodiment of the present invention. The developing portion 30 contains a toner or the like. The charging member 31 charges the photosensitive member 27. The transfer device 32 transfers the developed image to a recording medium 34. The conveying roller 33 conveys the recording medium 34. The recording medium 34 may be a paper sheet. The fuser 35 fixes the image formed on the recording medium.

Figure 4:
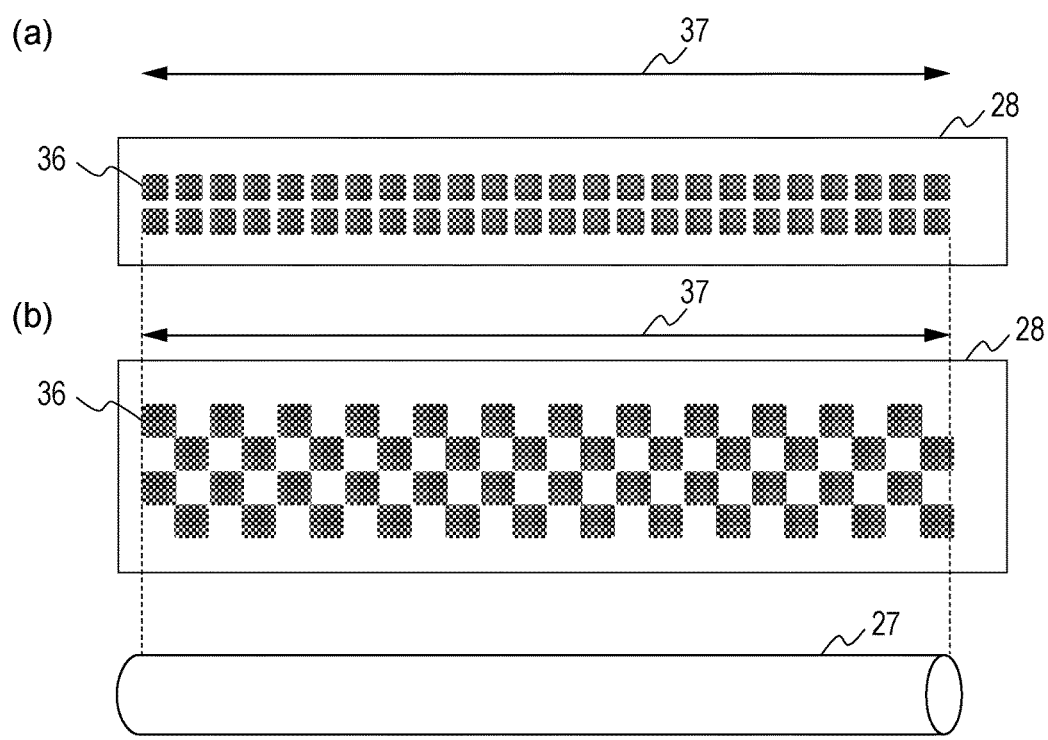
FIG. 4 is a schematic illustrative representation of exposure devices according to embodiments of the present invention.

FIG. 4 shows schematic illustrative representations (a) and (b) of exposure light sources 28 each having emitting portions 36 arranged on a long substrate. In each exposure light source, the organic light-emitting elements are arranged so as to extend in the direction indicated by arrows 37. This direction is the same as the direction of the rotation axis of the photosensitive member 27. This direction can be called the longitudinal axis direction of the photosensitive member.

Representation (a) of FIG. 4 shows a form of the photosensitive member in which the emitting portions are arranged along the longitudinal axis direction of the photosensitive member. Representation (b) of FIG. 4 shows a form different from the form of (a) and in which the emitting portions are arranged alternately in first rows and second rows. The emitting portions in the first rows and the emitting portions in the second rows are arranged at different positions in the column direction.

In each first row, the emitting portions are aligned so as to be separated from each other by spaces. In each second row, the emitting portions are disposed at positions corresponding to the spaces between each emitting portion in the first row. Thus, the emitting portions are arranged with spaces therebetween in the column direction as well.

In other words, the emitting portions of (b) in FIG. 4 are arranged, for example, in a matrix manner, in a staggered manner, or in a checker.

Figure 5:
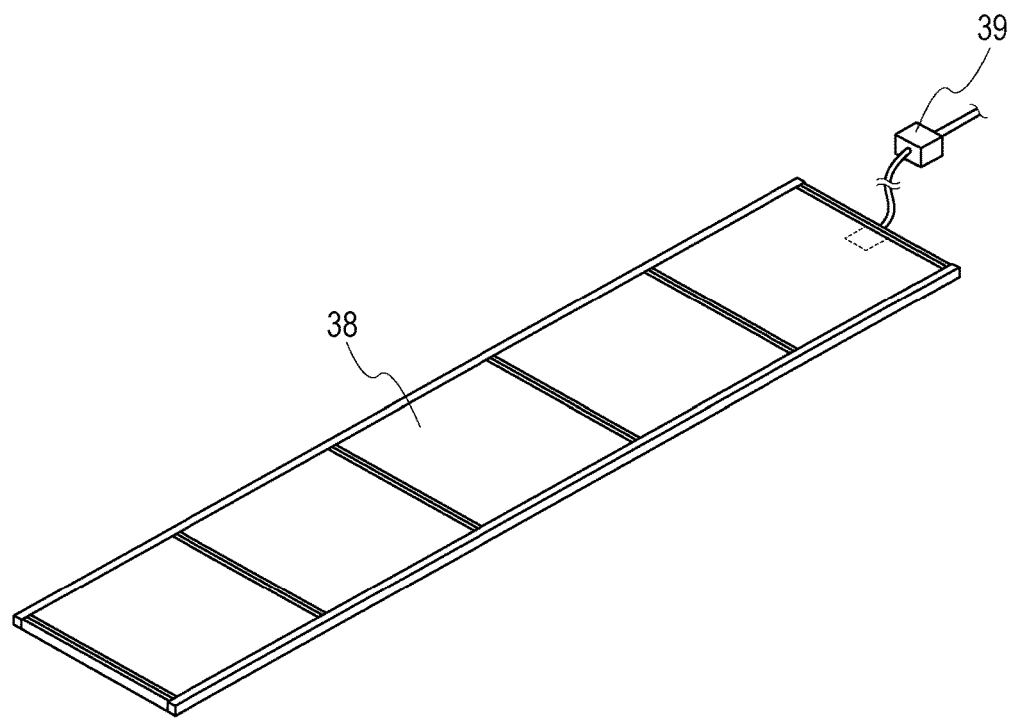
FIG. 5 is a schematic view of a lighting device according to an embodiment of the present invention.

FIG. 5 is a schematic view of a lighting device according to an embodiment of the present invention. The lighting device includes a substrate, organic light-emitting elements 38, and an AC/DC converter circuit 39. In addition, the substrate may be provided with a heat radiation portion (not shown) on the surface thereof opposite the organic light-emitting elements.

As described above, by operating the display device, lighting device or image forming apparatus including the organic light-emitting elements of an embodiment of the present invention, high-quality images can stably be displayed over a long time.

EXAMPLES

Example 1

Synthesis of Exemplified Compound A2

(1) Synthesis of Compound E3

[Chem. 16]

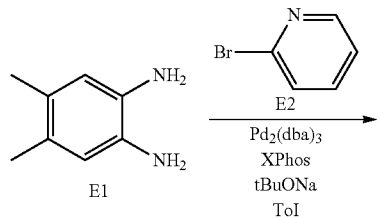

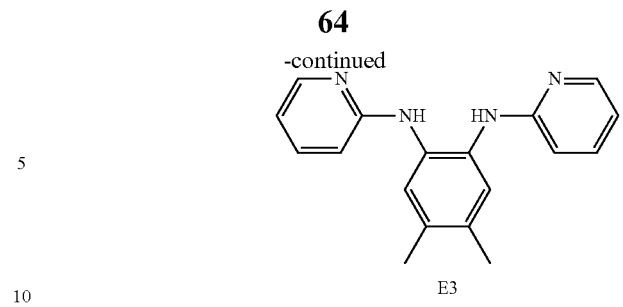

The following compounds and solvent were added to a 100 mL recovery flask:
E1: 1.36 g (10.0 mmol)
E2: 3.30 g (21.0 mmol)
Tris(dibenzylideneacetone)dipalladium (0): 274 mg (0.3 mmol)
2-Dicyclohexylphosphino-2',4',6'-triisopropylbiphenyl: 333 mg (0.7 mmol)
Sodium tert-butoxide: 2.31 g (24.0 mmol)
Toluene: 50 mL The mixture of these materials was heated to reflux with stirring for 8 hours. After the completion of the reaction, the reaction mixture was filtered through celite and then subjected to separation by adding water. The separated reaction product was purified by silica gel column chromatography (eluent: heptane/chloroform=3/1 to 2/1) to yield 1.77 g of Compound E3 (yield: 61%).

(2) Synthesis of Compound E4

[Chem. 17]

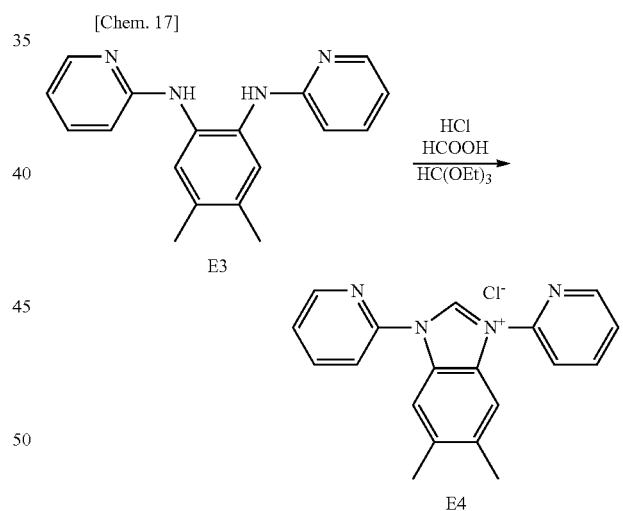

The following compounds and solvent were added to a 100 mL recovery flask:
E27: 1.45 g (5.00 mmol)
Triethyl orthoformate: 50 ml
To the solution of these materials, 0.8 mL of 12 N hydrochloric acid was added, and the mixture was stirred for 5 minutes. Then, 0.05 mL of formic acid was added, and the mixture was heated at 80° C. with stirring for 4 hours. After the completion of the reaction, 20 mL of diethyl ether was added to the cooled reaction mixture. Precipitated crystals were collected by filtration. After being washed with diethyl ether, the crystals were dried at 120° C. under reduced pressure to yield 1.51 g of Compound E4 (yield: 90%).

(2) Synthesis of Exemplified Compound A2

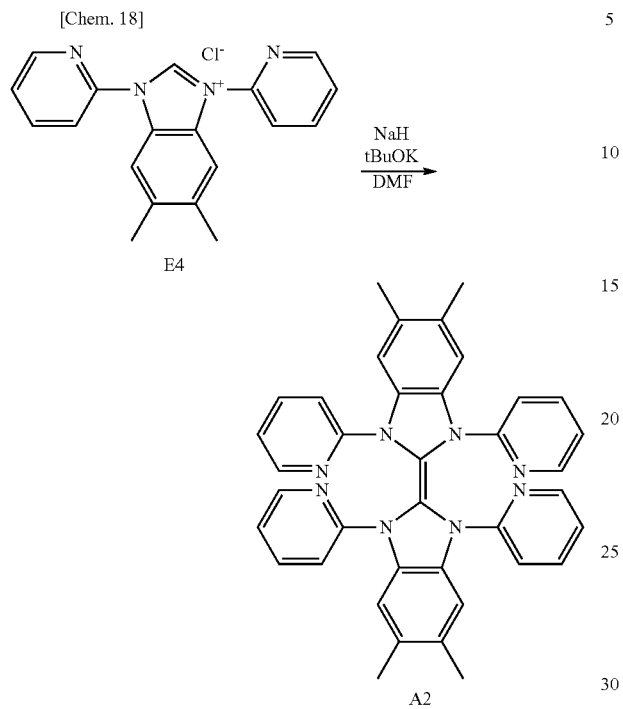

In a nitrogen flow, the following compound and solvent were added to a 100 mL recovery flask:

E4: 336 mg (1.00 mmol)
Dehydrated DMF: 5 mL

After degassing the solution of these materials, 96 mg (4.00 mmol) of sodium hydride was added, followed by stirring for 2 minutes. Then, 44 mg (0.4 mmol) of tBuOK was added, and the sample was heated at 30° C. with stirring for 24 hours. After the completion of the reaction, 10 mL of water degassed with nitrogen was gradually added to the sample with stirring to precipitate the reaction product, and then the solvent was removed using a syringe. After the operation of adding 10 mL of water degassed with nitrogen and then removing the solvent using the syringe was performed twice, 10 mL of degassed hexane was added, and the sample was washed and dispersed with ultrasonic waves. Then, the reaction product was collected by filtration through a membrane filter and washed with hexane. Thus 210 mg of yellow powder Exemplified Compound A2 was obtained (yield: 77%).

The resulting compound was subjected to matrix-assisted laser desorption/ionization time-of-flight mass spectrometry (MALDI-TOF-MS) using Autoflex LRF manufactured by Bruker.

Measured value: m/z=600.29; Calculated value: 600.27

CV measurement was performed in 0.1 M solution of tetrabutylammonium perchlorate in N,N-dimethylformamide with a Ag/Ag+ reference electrode, a Pt counter electrode, and a glassy carbon working electrode. The potential scan rate was 0.5 V/s.

For this measurement, an electrochemical analyzer Model 660C manufactured by ALS was used. Oxidation potential was −0.74V.

Example 2

Synthesis of Exemplified Compound A10

Exemplified compound A10 was synthesized in the same manner as in operation (1) of Example 1, except that Compound E5 shown below was used instead of Compound E1 and Compound E6 shown below was used instead of Compound E2.

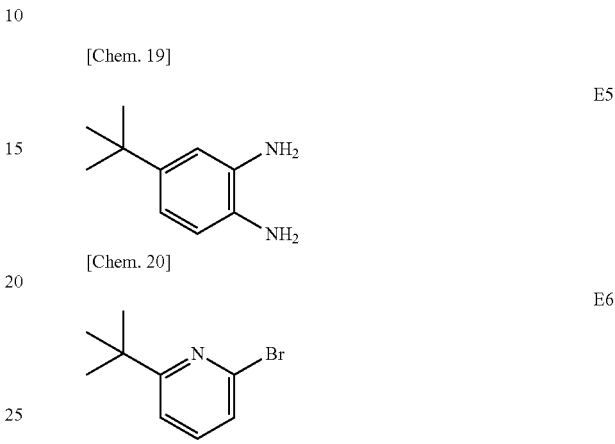

The resulting compound was identified as below.
The resulting compound was subjected to matrix-assisted laser desorption/ionization time-of-flight mass spectrometry (MALDI-TOF-MS) using Autoflex LRF manufactured by Bruker.

Measured value: m/z=881.02; Calculated value: 880.59
The oxidation potential measured with an electrochemical analyzer Model 660C manufactured by ALS was −0.81 V.

Example 3

Synthesis of Exemplified Compound A14

Exemplified compound A14 was synthesized in the same manner as in operation (1) of Example 1, except that Compound E7 shown below was used instead of Compound E2.

[Chem. 21]

The resulting compound was identified as below.
The resulting compound was subjected to matrix-assisted laser desorption/ionization time-of-flight mass spectrometry (MALDI-TOF-MS) using Autoflex LRF manufactured by Bruker.

Measured value: m/z=600.31; Calculated value: 600.27
The oxidation potential measured with an electrochemical analyzer Model 660C manufactured by ALS was −0.74 V.

Example 4

Synthesis of Exemplified Compound A19

Exemplified compound A19 was synthesized in the same manner as in operation (1) of Example 1, except that Compound E8 shown below was used instead of Compound E1 and Compound E9 shown below was used instead of Compound E2.

[Chem. 22]

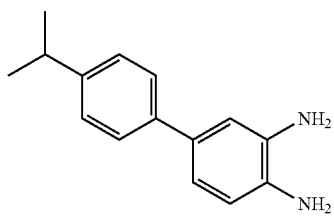
E8

[Chem. 23]

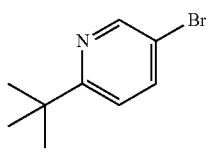
E9

The resulting compound was identified as below.
The resulting compound was subjected to matrix-assisted laser desorption/ionization time-of-flight mass spectrometry (MALDI-TOF-MS) using Autoflex LRF manufactured by Bruker.
Measured value: m/z=1033.66; Calculated value: 1032.65
The oxidation potential measured with an electrochemical analyzer Model 660C manufactured by ALS was −0.83 V.

Example 5

Synthesis of Exemplified Compound A20

Exemplified compound A20 was synthesized in the same manner as in operation (1) of Example 1, except that Compound E10 shown below was used instead of Compound E1 and Compound E9 shown above was used instead of Compound E2.

[Chem. 24]

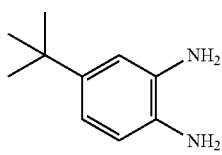
E10

The resulting compound was identified as below.
The resulting compound was subjected to matrix-assisted laser desorption/ionization time-of-flight mass spectrometry (MALDI-TOF-MS) using Autoflex LRF manufactured by Bruker.
Measured value: m/z=880.79; Calculated value: 880.59
The oxidation potential measured with an electrochemical analyzer Model 660C manufactured by ALS was −0.85 V.

Example 6

Synthesis of Exemplified Compound A35

Exemplified compound A35 was synthesized in the same manner as in operation (1) of Example 1, except that Compound E10 shown above was used instead of Compound E1 and Compound E11 shown below was used instead of Compound E2.

[Chem. 25]

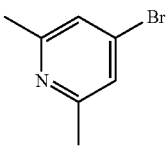
E11

The resulting compound was identified as below.
The resulting compound was subjected to matrix-assisted laser desorption/ionization time-of-flight mass spectrometry (MALDI-TOF-MS) using Autoflex LRF manufactured by Bruker.
Measured value: m/z=768.68; Calculated value: 768.46
The oxidation potential measured with an electrochemical analyzer Model 660C manufactured by ALS was −0.75 V.

Example 7

Synthesis of Exemplified Compound A37

Exemplified compound A37 was synthesized in the same manner as in operation (1) of Example 1, except that Compound E12 shown below was used instead of Compound E1 and Compound E13 shown below was used instead of Compound E2.

[Chem. 26]

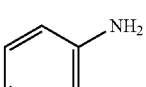
E12

[Chem. 27]

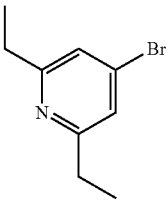
E13

The resulting compound was identified as below.
The resulting compound was subjected to matrix-assisted laser desorption/ionization time-of-flight mass spectrometry (MALDI-TOF-MS) using Autoflex LRF manufactured by Bruker.
Measured value: m/z=768.64; Calculated value: 768.46
The oxidation potential measured with an electrochemical analyzer Model 660C manufactured by ALS was −0.71 V.

Example 8

Synthesis of Exemplified Compound A43

Exemplified compound A43 was synthesized in the same manner as in operation (1) of Example 1, except that Compound E10 shown above was used instead of Compound E1 and Compound E14 shown below was used instead of Compound E2.

[Chem. 28]

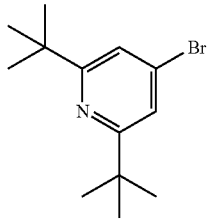

E14

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=1105.14; Calculated value: 1104.84

The oxidation potential measured with an electrochemical analyzer Model 660C manufactured by ALS was −0.68 V.

Example 9

Synthesis of Exemplified Compound B3

Exemplified compound B3 was synthesized in the same manner as in operation (1) of Example 1, except that Compound E10 shown above was used instead of Compound E1 and Compound E15 shown below was used instead of Compound E2.

[Chem. 29]

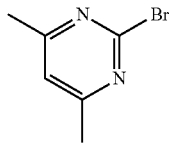

E15

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=772.86; Calculated value: 772.44

The oxidation potential measured with an electrochemical analyzer Model 660C manufactured by ALS was −0.81 V.

Example 10

Synthesis of Exemplified Compound B16

Exemplified compound B16 was synthesized in the same manner as in operation (1) of Example 1, except that Compound E10 shown above was used instead of Compound E1 and Compound E16 shown below was used instead of Compound E2.

[Chem. 30]

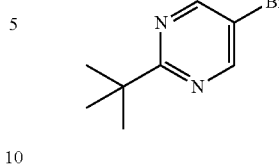

E16

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=884.87; Calculated value: 884.57

The oxidation potential measured with an electrochemical analyzer Model 660C manufactured by ALS was −0.67 V.

Example 11

Synthesis of Exemplified Compound D16

Exemplified compound D16 was synthesized in the same manner as in operation (1) of Example 1, except that Compound E17 shown below was used instead of Compound E2.

[Chem. 31]

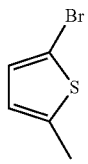

E17

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=676.22; Calculated value: 676.18

The oxidation potential measured with an electrochemical analyzer Model 660C manufactured by ALS was −0.90 V.

Example 12

Synthesis of Exemplified Compound D19

Exemplified compound D19 was synthesized in the same manner as in operation (1) of Example 1, except that Compound E10 shown above was used instead of Compound E1 and Compound E19 shown below was used instead of Compound E2.

[Chem. 32]

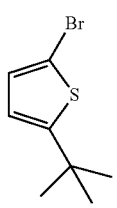

E19

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=900.57; Calculated value: 900.43

The oxidation potential measured with an electrochemical analyzer Model 660C manufactured by ALS was −0.89 V.

Example 13

Synthesis of Exemplified Compound D20

Exemplified compound D20 was synthesized in the same manner as in operation (1) of Example 1, except that Compound E20 shown below was used instead of Compound E2.

[Chem. 33]

E20

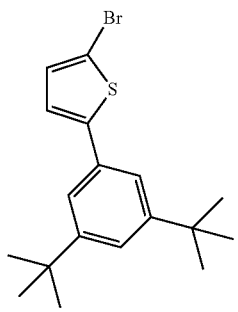

Organic compound layers and an electrode layer, shown in Table 2, were continuously formed on the substrate. At this time, the opposing electrode (metal electrode layer or cathode) was formed with an area of 3 mm$^2$.

TABLE 2

|  | Material | Thickness (nm) |
| --- | --- | --- |
| Hole transport layer | G-1 | 30 |
| Electron blocking layer | G-2 | 10 |
| Luminescent layer | G-3 (Host) | 30 |
|  | G-4 (Guest) |  |
|  | (G-3:G-4 = 98:2 (weight ratio)) |  |
| Hole blocking layer | G-5 | 10 |
| Electron transport layer | G-6 | 15 |
| Electron injection layer | G-7 | 15 |
|  | G-8 |  |
|  | (G-7:G-8 = 50:50 (weight ratio)) |  |
| Metal electrode layer | Al | 100 |

Before forming the metal electrode layer, the sample was allowed to stand in the air for 10 minutes and then the metal electrode layer was formed.

Materials G1 to G7 used in each Example were shown in Table 3. Material G 8 was a 2,2'-bibenzo[d]imidazolidene compound having heteromonocyclic groups at the 1-, 1'-, 3- and 3'-positions or Comparative Compound (3) or (4), as shown in Table 3.

TABLE 3

| | G1 | G2 | G3 | G4 | G5 | G6 | G7 | G8 | Light Emission |
| --- | --- | --- | --- | --- | --- | --- | --- | --- | --- |
| Example 14 | HT1 | HT7 | EM13 | RD1 | ET2 | ET2 | EI6 | A10 | good |
| Example 15 | HT1 | HT7 | EM13 | RD1 | ET2 | ET2 | EI6 | A35 | good |
| Comparative Example 1 | HT1 | HT7 | EM13 | RD1 | ET2 | ET2 | EI6 | Comparative compound 3 | Bad |
| Comparative Example 2 | HT1 | HT7 | EM13 | RD1 | ET2 | ET2 | EI6 | Comparative compound 4 | Bad |

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=1372.99; Calculated value: 1372.75

The oxidation potential measured with an electrochemical analyzer Model 660C manufactured by ALS was −0.90 V.

Examples 14-15

Each organic light-emitting element was produced by forming an anode, a hole transport layer, an electron blocking layer, a luminescent layer, a hole blocking layer, an electron transport layer, and a cathode in that order on a substrate.

First, an ITO layer was formed on a glass substrate and then patterned into an ITO electrode (anode). The thickness of the ITO electrode was 100 nm. The resulting substrate having the ITO electrode thereon was used in the subsequent step.

Light emission from each element was examined at a voltage of 8 V. As a result, the elements using the present organic compound emitted light, but the elements using Comparative Compound (3) or (4) did not emit light.

This is probably because the Comparative Compounds deteriorated when the element was exposed to the air, thus losing the electron injectability thereof.

Examples 16-24

Each organic light-emitting element was produced by forming an anode, a hole transport layer, an electron blocking layer, a luminescent layer, a hole blocking layer, an electron transport layer, and a cathode in that order on a substrate.

First, an ITO layer was formed on a glass substrate and then patterned into an ITO electrode (anode). The thickness of the ITO electrode was 100 nm. The resulting substrate having the ITO electrode thereon was used in the subsequent step.

Organic compound layers and an electrode layer, shown in Table 4, were continuously formed on the substrate. At this time, the opposing electrode (metal electrode layer or cathode) was formed with an area of 3 mm².

TABLE 4

|  | Material | Thickness (nm) |
|---|---|---|
| Hole transport layer | G-1 | 30 |
| Electron blocking layer | G-2 | 10 |
| Luminescent layer | G-3 (Host) G-4 (Guest) (G-3:G-4 = 98:2 (weight ratio)) | 30 |
| Hole blocking layer | G-5 | 10 |
| Electron transport layer | G-6 | 15 |
| Electron injection layer | G-7 G-8 (G-7:G-8 = 50:50 (weight ratio)) | 15 |
| Metal electrode layer | G-9 | 100 |

Materials G1 to G7 used in each Example were shown in Table 5. Material G 8 was a 2,2'-bibenzo[d]imidazolidene compound having heteromonocyclic groups at the 1-, 1'-, 3- and 3'-positions, as shown in Table 5.

TABLE 5

|  | G1 | G2 | G3 | G4 | G5 | G6 | G7 | G8 | G9 | Emission efficiency (cd/A) | Voltage (V) |
|---|---|---|---|---|---|---|---|---|---|---|---|
| Example 16 | HT2 | HT7 | EM12 | RD1 | ET10 | EI6 | EI6 | A2 | Al | 4 | 4 |
| Example 17 | HT2 | HT7 | EM12 | RD1 | ET10 | EI16 | EI8 | A3 | Ag | 4 | 4 |
| Example 18 | HT2 | HT7 | EM12 | RD1 | ET10 | EI16 | EI8 | A10 | Au | 4 | 5 |
| Example 19 | HT6 | HT8 | EM4 | GD4 | EM6 | EI6 | EI14 | A14 | Ag:Mg = 1:1 | 21 | 6 |
| Example 20 | HT2 | HT8 | EM3 | BD4 | ET4 | EI14 | EI8 | A20 | Ag | 5 | 5 |
| Example 21 | HT6 | HT8 | EM4 | GD4 | EM6 | EI6 | EI18 | A35 | Ag | 20 | 6 |
| Example 22 | HT6 | HT7 | EM8 | RD4 | ET6 | EI7 | EI8 | A43 | Ag:Mg = 1:1 | 4 | 5 |
| Example 23 | HT2 | HT7 | EM14 | RD2 | ET9 | EI8 | EI14 | B3 | Ag | 5 | 5 |
| Example 24 | HT2 | HT7 | EM4 | BD7 | EI9 | EI18 | EI18 | D16 | Ag:Cu = 5:1 | 5 | 5 |

Examples 25-29

Each organic light-emitting element was produced by forming an anode, a hole transport layer, an electron blocking layer, a luminescent layer, a hole blocking layer, an electron transport layer, and a cathode in that order on a substrate.

First, an ITO layer was formed on a glass substrate and then patterned into an ITO electrode (anode). The thickness of the ITO electrode was 100 nm. The resulting substrate having the ITO electrode thereon was used in the subsequent step.

Organic compound layers and an electrode layer, shown in Table 6, were continuously formed on the substrate. At this time, the opposing electrode (metal electrode layer or cathode) was formed with an area of 3 mm².

TABLE 6

|  | Material | Thickness (nm) |
|---|---|---|
| Hole transport layer | G-1 | 30 |
| Electron blocking layer | G-2 | 10 |
| Luminescent layer | G-3 (Host) | 30 |
|  | G-4 (Guest) |  |
|  | (G-3:G-4 = 98:2 (weight ratio)) |  |
| Hole blocking layer | G-5 | 10 |
| Electron transport layer | G-6 | 26 |
| Electron injection layer | G-8 | 4 |
| Metal electrode layer | G-9 | 100 |

Materials G1 to G6 used in each Example were shown in Table 7. Material G 8 was a 2,2'-bibenzo[d]imidazolidene compound having heteromonocyclic groups at the 1-, 1'-, 3- and 3'-positions. Material G9 was a metal shown in Table 7. If metals were mixed, the proportions thereof were shown on a weight basis. Thus prepared samples were examined.

TABLE 7

|  | G1 | G2 | G3 | G4 | G5 | G6 | G8 | G9 | Emission efficiency (cd/A) | Voltage (V) |
|---|---|---|---|---|---|---|---|---|---|---|
| Example 25 | HT6 | HT7 | EM13 | RD1 | EI6 | EI6 | A13 | Ag:Mg = 1:1 | 4 | 4 |
| Example 26 | HT2 | HT7 | EM12 | RD1 | ET10 | EI16 | A29 | Ag | 4 | 4 |
| Example 27 | HT2 | HT8 | EM7 | GD6 | EI4 | EI17 | A42 | Au | 24 | 6 |
| Example 28 | HT2 | HT8 | EM14 | RD1 | EI14 | EI14 | B16 | Ag | 4 | 3 |
| Example 29 | HT1 | HT7 | EM8 | BD8 | EI4 | EI12 | D19 | Al | 5 | 5 |

As described above, by using a 2,2'-bibenzo[d]imidazolidene compound having heteromonocyclic groups at the 1-, 1'-, 3- and 3'-positions according to an embodiment of the present invention in the electron injection layer of an organic light-emitting element, the organic light-emitting element can be stable in the air.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A 2,2'-bibenzo[d]imidazolidene compound expressed by the following general formula (1):

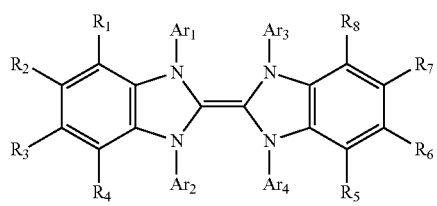

[1]

wherein $Ar_1$ to $Ar_4$ each represent a substituted or unsubstituted heteromonocyclic group; $R_1$ to $R_8$ each represent a hydrogen atom or a substituent selected from the group consisting of halogen atoms, alkyl groups having a carbon number in the range of 1 to 8, and substituted or unsubstituted aromatic hydrocarbon groups.

2. The 2,2'-bibenzo[d]imidazolidene compound according to claim 1, wherein each of the heteromonocyclic groups is a 6-membered aromatic ring including at least one carbon atom and at least one nitrogen atom or a 5-membered ring including at least one carbon atom and at least one of nitrogen, sulfur, and oxygen atoms.

3. The 2,2'-bibenzo[d]imidazolidene compound according to claim 2, wherein each of the heteromonocyclic groups includes a single nitrogen atom.

4. The 2,2'-bibenzo[d]imidazolidene compound according to claim 2, wherein each of the heteromonocyclic groups includes two nitrogen atoms.

5. The 2,2'-bibenzo[d]imidazolidene compound according to claim 2, wherein each of the heteromonocyclic groups includes three nitrogen atoms.

6. The 2,2'-bibenzo[d]imidazolidene compound according to claim 1, wherein $Ar_1$ to $Ar_4$ represent the same substituent.

7. An organic element comprising:
a pair of electrodes; and
an organic compound layer disposed between the pair of electrodes, the organic compound layer containing the 2,2'-benzo[d]imidazolidene compound as set forth in claim 1.

8. An organic light-emitting element comprising:
an anode;
a cathode;
a luminescent layer disposed between the anode and the cathode, and
an organic compound layer disposed between the cathode and the luminescent layer, the organic compound layer containing the 2,2'-bibenzo[d]imidazolidene compound as set forth in claim 1.

9. The organic light-emitting element according to claim 8, wherein the organic compound layer contains an additional organic compound.

10. The organic light-emitting element according to claim 9, wherein the additional organic compound has a higher oxidation potential than the 2,2'-bibenzo[d]imidazolidene compound.

11. The organic light-emitting element according to claim 9, wherein the proportion of the additional organic compound to the total weight of the additional organic compound and the 2,2'-bibenzo[d]imidazolidene compound is in the range of higher than 0% by weight to 80% by weight.

12. The organic light-emitting element according to claim 9, wherein the organic compound layer is in contact with the cathode.

13. A display device comprising:
a plurality of light-emitting pixels, each including an organic light-emitting element as set forth in claim 9 and an active element connected to the organic light-emitting element.

14. The display device according to claim 13, wherein the active element is a transistor having an active region containing an oxide semiconductor.

15. An image information processing apparatus, comprising:
a display portion on which an image is displayed;
an input portion to which image information is input; and
a processing portion adapted to process the image information,
wherein the display portion is the display device as set forth in claim 13.

16. A lighting device comprising:
an organic light-emitting element as set forth in claim 8; and
an AC/DC converter connected to the organic light-emitting element.

17. A lighting device comprising:
a substrate;
a heat radiation portion; and
an organic light-emitting element as set forth in claim 8;
wherein the heat radiation portion dissipates heat from the lighting device.

18. An image forming apparatus comprising:
a photosensitive member;
an exposure portion adapted to expose the photosensitive member;
a charging member adapted to charge the photosensitive member; and
a developing portion adapted to apply a developer to the photosensitive member, wherein the exposure portion includes the organic light-emitting element as set forth in claim 8.

19. An exposure device adapted to expose a photosensitive member, the exposure device comprising:
the organic light-emitting elements as set forth in claim 8, and
the organic light-emitting elements being arranged in a line along the longitudinal direction of the photosensitive member.

20. A sensor device comprising:
a pair of electrodes;
a photoelectric conversion portion disposed between the pair of electrodes; and
a plurality of transistors each connected to one of the electrodes,
wherein the photoelectric conversion portion contains the 2,2'-bibenzo[d]imidazolidene compound as set forth in claim 1.

* * * * *